(12) United States Patent
Dewey et al.

(10) Patent No.: US 11,850,163 B2
(45) Date of Patent: Dec. 26, 2023

(54) INTERBODY IMPLANT WITH ADJUSTING SHIMS

(71) Applicant: Warsaw Orthopedic, Inc., Warsaw, IN (US)

(72) Inventors: Jonathan M. Dewey, Memphis, TN (US); Richard A. Hynes, Melbourne Beach, FL (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 17/590,529

(22) Filed: Feb. 1, 2022

(65) Prior Publication Data
US 2023/0240857 A1    Aug. 3, 2023

(51) Int. Cl.
*A61F 2/44* (2006.01)
*A61F 2/30* (2006.01)
*A61F 2/28* (2006.01)

(52) U.S. Cl.
CPC .... *A61F 2/4455* (2013.01); *A61F 2002/2835* (2013.01); *A61F 2002/30331* (2013.01);
(Continued)

(58) Field of Classification Search
CPC ................ A61F 2250/0004–2250/001; A61F 2250/0048; A61F 2002/30331;
(Continued)

(56) References Cited

U.S. PATENT DOCUMENTS 4,553,273 A    11/1985  Wu
4,636,217 A    1/1987   Ogilvie et al.
(Continued)

FOREIGN PATENT DOCUMENTS

DE    44 16 605 C1    6/1995
EP    0 767 636 A1    4/1997
(Continued)

OTHER PUBLICATIONS

International Search Report, and Written Opinion for Application. No. PCT/US2019/019067, dated Jun. 3, 2019.
(Continued)

*Primary Examiner* — Julianna N Harvey
*Assistant Examiner* — Angel Roberto Mora-Velazquez
(74) *Attorney, Agent, or Firm* — FOX ROTHSCHILD LLP

(57) ABSTRACT

An expandable implant may include a superior endplate and an inferior endplate. The superior endplate may have at least one track extending in a proximal-to-distal direction and an inferior endplate may have at least one track extending in the proximal-to-distal direction. An adjusting shim may be disposed within the at least one track to adjust a spacing and angle of inclination of the implant. Some embodiments may include a plurality of tracks for adjusting a spacing and an angle of inclination between the superior endplate and the inferior endplate. Some embodiments may be configured to adjust an orientation of the implant relative to a disc space in both the sagittal plane and the coronal plane. Various embodiments disclosed herein may be used in an Anterior lumbar interbody fusion (ALIF), Transforaminal lumbar interbody fusion (TLIF), or a lateral Lumbar Interbody Fusion (LLIF) procedure, for example.

20 Claims, 27 Drawing Sheets

(52) U.S. Cl.
CPC .............. *A61F 2002/30578* (2013.01); *A61F 2002/30579* (2013.01)

(58) Field of Classification Search
CPC .. A61F 2002/30383; A61F 2002/30359; A61F 2002/30375; A61F 2002/30398; A61F 2002/304; A61F 2002/30401; A61F 2002/2835; A61F 2/4455; A61F 2002/30579
See application file for complete search history.

(56) References Cited

U.S. PATENT DOCUMENTS

| | | |
|---|---|---|
| 4,759,769 A | 7/1988 | Hedman et al. |
| 5,059,193 A | 10/1991 | Kuslich |
| 5,171,278 A | 12/1992 | Pisharodi |
| 5,336,223 A | 8/1994 | Rogers |
| 5,390,683 A | 2/1995 | Pisharodi |
| 5,522,899 A | 6/1996 | Michelson |
| 5,554,191 A | 9/1996 | Lahille et al. |
| 5,575,790 A | 11/1996 | Chen et al. |
| 5,609,635 A | 3/1997 | Michelson |
| 5,653,762 A | 8/1997 | Pisharodi |
| 5,658,336 A | 8/1997 | Pisharodi |
| 5,665,122 A | 9/1997 | Kambin |
| 5,693,100 A | 12/1997 | Pisharodi |
| 5,697,977 A | 12/1997 | Pisharodi |
| 5,702,391 A | 12/1997 | Lin |
| 5,702,453 A | 12/1997 | Rabbe et al. |
| 5,702,455 A | 12/1997 | Saggar |
| 5,797,918 A | 8/1998 | McGuire et al. |
| 5,800,550 A | 9/1998 | Sertich |
| 5,865,848 A | 2/1999 | Baker |
| 5,893,890 A | 4/1999 | Pisharodi |
| 5,931,777 A | 8/1999 | Sava |
| 5,941,885 A | 8/1999 | Jackson |
| 5,971,987 A | 10/1999 | Huxel et al. |
| 5,980,522 A | 11/1999 | Koros et al. |
| 6,045,579 A | 4/2000 | Hochshuler et al. |
| 6,074,343 A | 6/2000 | Nathanson et al. |
| 6,080,193 A | 6/2000 | Hochshuler et al. |
| 6,099,531 A | 8/2000 | Bonutti |
| 6,102,949 A | 8/2000 | Biedermann et al. |
| 6,102,950 A | 8/2000 | Vaccaro |
| 6,106,557 A | 8/2000 | Robioneck et al. |
| 6,113,638 A | 9/2000 | Williams et al. |
| 6,117,174 A | 9/2000 | Nolan |
| 6,132,465 A | 10/2000 | Ray et al. |
| 6,159,211 A | 12/2000 | Boriani et al. |
| 6,159,244 A | 12/2000 | Suddaby |
| 6,176,882 B1 | 1/2001 | Biedermann et al. |
| 6,179,873 B1 | 1/2001 | Zientek |
| 6,190,414 B1 | 2/2001 | Young et al. |
| 6,193,757 B1 | 2/2001 | Foley et al. |
| 6,217,579 B1 | 4/2001 | Koros |
| 6,245,108 B1 | 6/2001 | Biscup |
| 6,309,421 B1 | 10/2001 | Pisharodi |
| 6,342,074 B1 | 1/2002 | Simpson |
| 6,371,989 B1 | 4/2002 | Chauvin et al. |
| 6,395,031 B1 | 5/2002 | Foley et al. |
| 6,423,063 B1 | 7/2002 | Bonutti |
| 6,432,106 B1 | 8/2002 | Fraser |
| 6,436,140 B1 | 8/2002 | Liu et al. |
| 6,443,989 B1 | 9/2002 | Jackson |
| 6,443,990 B1 | 9/2002 | Aebi et al. |
| 6,454,806 B1 | 9/2002 | Cohen et al. |
| 6,454,807 B1 | 9/2002 | Jackson |
| 6,461,359 B1 | 10/2002 | Tribus et al. |
| 6,491,724 B1 | 12/2002 | Ferree |
| 6,520,991 B2 | 2/2003 | Huene |
| 6,520,993 B2 | 2/2003 | James et al. |
| 6,527,803 B1 | 3/2003 | Crozet et al. |
| 6,562,074 B2 | 5/2003 | Gerbec et al. |
| 6,576,016 B1 | 6/2003 | Hochshuler et al. |
| 6,623,525 B2 | 9/2003 | Ralph et al. |
| 6,629,998 B1 | 10/2003 | Lin |
| 6,635,086 B2 | 10/2003 | Lin |
| 6,648,917 B2 | 11/2003 | Gerbec et al. |
| 6,676,703 B2 | 1/2004 | Biscup |
| 6,685,742 B1 | 2/2004 | Jackson |
| 6,723,126 B1 | 4/2004 | Berry |
| 6,770,096 B2 | 8/2004 | Bolger et al. |
| 6,773,460 B2 | 8/2004 | Jackson |
| 6,821,298 B1 | 11/2004 | Jackson |
| 6,835,206 B2 | 12/2004 | Jackson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,923,814 B1 | 8/2005 | Hildebrand et al. |
| 6,926,737 B2 | 8/2005 | Jackson |
| 6,953,477 B2 | 10/2005 | Berry |
| 6,964,687 B1 | 11/2005 | Bernard et al. |
| 6,974,480 B2 | 12/2005 | Messerli et al. |
| 6,984,234 B2 | 1/2006 | Bray |
| 7,112,222 B2 | 9/2006 | Fraser et al. |
| 7,135,043 B2 | 11/2006 | Nakahara et al. |
| 7,137,997 B2 | 11/2006 | Paul |
| 7,172,627 B2 | 2/2007 | Fiere et al. |
| 7,188,626 B2 | 3/2007 | Foley et al. |
| 7,204,853 B2 | 4/2007 | Gordon et al. |
| 7,232,464 B2 | 6/2007 | Mathieu et al. |
| 7,238,203 B2 | 7/2007 | Bagga et al. |
| 7,255,700 B2 | 8/2007 | Kaiser et al. |
| 7,316,532 B2 | 1/2008 | Matthys-Mark |
| 7,316,714 B2 | 1/2008 | Gordon et al. |
| 7,407,483 B2 | 8/2008 | Perez-Cruet et al. |
| 7,481,766 B2 | 1/2009 | Lee et al. |
| 7,491,168 B2 | 2/2009 | Raymond et al. |
| 7,537,565 B2 | 5/2009 | Bass |
| 7,618,456 B2 | 11/2009 | Mathieu et al. |
| 7,625,394 B2 | 12/2009 | Molz, IV et al. |
| 7,655,046 B2 | 2/2010 | Dryer et al. |
| 7,678,148 B2 | 3/2010 | Peterman |
| 7,703,727 B2 | 4/2010 | Selness |
| 7,708,778 B2 | 5/2010 | Gordon et al. |
| 7,708,779 B2 | 5/2010 | Edie et al. |
| 7,727,280 B2 | 6/2010 | McLuen |
| 7,753,958 B2 | 7/2010 | Gordon et al. |
| 7,780,594 B2 | 8/2010 | Hutton |
| 7,806,932 B2 | 10/2010 | Webb et al. |
| 7,815,682 B1 | 10/2010 | Peterson et al. |
| 7,819,801 B2 | 10/2010 | Miles et al. |
| 7,824,428 B2 | 11/2010 | Mikkonen et al. |
| 7,828,849 B2 | 11/2010 | Lim |
| 7,846,167 B2 | 12/2010 | Garcia et al. |
| 7,846,207 B2 | 12/2010 | Lechmann et al. |
| 7,850,731 B2 | 12/2010 | Brittan et al. |
| 7,850,733 B2 | 12/2010 | Baynham et al. |
| 7,862,616 B2 | 1/2011 | Lechmann et al. |
| 7,875,076 B2 | 1/2011 | Mathieu et al. |
| 7,892,173 B2 | 2/2011 | Miles et al. |
| 7,909,869 B2 | 3/2011 | Gordon et al. |
| 7,914,559 B2 | 3/2011 | Carls et al. |
| 7,967,821 B2 | 6/2011 | Sicvol et al. |
| 7,981,031 B2 | 7/2011 | Frasier et al. |
| 8,016,836 B2 | 9/2011 | Corrao et al. |
| 8,062,375 B2 | 11/2011 | Glerum et al. |
| 8,105,382 B2 | 1/2012 | Olmos et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,147,550 B2 | 4/2012 | Gordon et al. |
| 8,172,903 B2 | 5/2012 | Gordon et al. |
| 8,182,539 B2 | 5/2012 | Tyber et al. |
| 8,257,442 B2 | 9/2012 | Edie et al. |
| 8,262,570 B2 | 9/2012 | White et al. |
| 8,262,662 B2 | 9/2012 | Beardsley et al. |
| 8,287,597 B1 | 10/2012 | Pimenta et al. |
| 8,303,498 B2 | 11/2012 | Miles et al. |
| 8,303,658 B2 | 11/2012 | Peterman |
| 8,303,663 B2 | 11/2012 | Jimenez et al. |
| 8,317,866 B2 | 11/2012 | Palmatier et al. |
| 8,323,185 B2 | 12/2012 | Perez-Cruet et al. |
| 8,328,872 B2 | 12/2012 | Duffield et al. |

(56) References Cited

U.S. PATENT DOCUMENTS

| | | |
|---|---|---|
| 8,343,048 B2 | 1/2013 | Warren, Jr. |
| 8,353,826 B2 | 1/2013 | Weiman |
| 8,355,780 B2 | 1/2013 | Miles et al. |
| 8,382,842 B2 | 2/2013 | Greenhalgh et al. |
| 8,388,527 B2 | 3/2013 | Miles et al. |
| 8,398,713 B2 | 3/2013 | Weiman |
| 8,403,990 B2 | 3/2013 | Dryer et al. |
| 8,419,797 B2 | 4/2013 | Biedermann et al. |
| 8,425,528 B2 | 4/2013 | Berry et al. |
| 8,435,298 B2 | 5/2013 | Weiman |
| 8,480,576 B2 | 7/2013 | Sandhu |
| 8,496,706 B2 | 7/2013 | Ragab et al. |
| 8,500,634 B2 | 8/2013 | Miles et al. |
| 8,506,635 B2 | 8/2013 | Palmatier et al. |
| 8,517,935 B2 | 8/2013 | Marchek et al. |
| 8,518,120 B2 | 8/2013 | Glerum et al. |
| 8,535,380 B2 | 9/2013 | Greenhalgh et al. |
| 8,550,994 B2 | 10/2013 | Miles et al. |
| 8,556,808 B2 | 10/2013 | Miles et al. |
| 8,556,979 B2 | 10/2013 | Glerum et al. |
| 8,579,809 B2 | 11/2013 | Parker |
| 8,579,979 B2 | 11/2013 | Edie et al. |
| 8,579,981 B2 | 11/2013 | Lim et al. |
| 8,602,984 B2 | 12/2013 | Raymond et al. |
| 8,608,785 B2 | 12/2013 | Reed et al. |
| 8,628,576 B2 | 1/2014 | Triplett et al. |
| 8,628,578 B2 | 1/2014 | Miller et al. |
| 8,632,595 B2 | 1/2014 | Weiman |
| 8,641,768 B2 | 2/2014 | Duffield et al. |
| 8,647,386 B2 | 2/2014 | Gordon et al. |
| 8,663,329 B2 | 3/2014 | Ernst |
| 8,668,419 B2 | 3/2014 | Hardt et al. |
| 8,668,715 B2 | 3/2014 | Sandhu |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,559 B2 | 4/2014 | Miles et al. |
| 8,709,083 B2 | 4/2014 | Duffield et al. |
| 8,709,085 B2 | 4/2014 | Lechmann et al. |
| 8,709,086 B2 | 4/2014 | Glerum |
| 8,715,353 B2 | 5/2014 | Bagga et al. |
| 8,740,983 B1 | 6/2014 | Arnold et al. |
| 8,753,271 B1 | 6/2014 | Miles et al. |
| 8,753,396 B1 | 6/2014 | Hockett et al. |
| 8,764,649 B2 | 7/2014 | Miles et al. |
| 8,771,360 B2 | 7/2014 | Jimenez et al. |
| 8,778,025 B2 | 7/2014 | Ragab et al. |
| 8,778,027 B2 | 7/2014 | Medina |
| 8,795,366 B2 | 8/2014 | Varela |
| 8,808,305 B2 | 8/2014 | Kleiner |
| 8,827,902 B2 | 9/2014 | Dietze, Jr. et al. |
| 8,828,085 B1 | 9/2014 | Jensen |
| 8,840,668 B1 | 9/2014 | Donahoe et al. |
| 8,845,731 B2 | 9/2014 | Weiman |
| 8,845,732 B2 | 9/2014 | Weiman |
| 8,845,734 B2 | 9/2014 | Weiman |
| 8,852,252 B2 | 10/2014 | Venturini et al. |
| 8,852,282 B2 | 10/2014 | Farley et al. |
| 8,864,833 B2 | 10/2014 | Glerum et al. |
| 8,882,813 B2 | 11/2014 | Jones et al. |
| 8,888,853 B2 | 11/2014 | Glerum et al. |
| 8,894,708 B2 | 11/2014 | Thalgott et al. |
| 8,894,711 B2 | 11/2014 | Varela |
| 8,894,712 B2 | 11/2014 | Varela |
| 8,906,095 B2 | 12/2014 | Christensen et al. |
| 8,920,500 B1 | 12/2014 | Pimenta et al. |
| 8,926,704 B2 | 1/2015 | Glerum et al. |
| 8,936,641 B2 | 1/2015 | Cain |
| 8,940,049 B1 | 1/2015 | Jimenez et al. |
| 8,968,363 B2 | 3/2015 | Weiman et al. |
| 8,986,344 B2 | 3/2015 | Sandhu |
| 8,992,425 B2 | 3/2015 | Karpowicz et al. |
| 8,992,544 B2 | 3/2015 | Sasing |
| 9,005,292 B2 | 4/2015 | Melamed |
| 9,005,293 B2 | 4/2015 | Moskowitz et al. |
| 9,005,295 B2 | 4/2015 | Kueenzi et al. |
| 9,017,412 B2 | 4/2015 | Wolters et al. |
| 9,034,045 B2 | 5/2015 | Davenport et al. |
| 9,050,146 B2 | 6/2015 | Woolley et al. |
| 9,050,194 B2 | 6/2015 | Thibodeau |
| 9,060,877 B2 | 6/2015 | Kleiner |
| 9,072,563 B2 | 7/2015 | Garcia et al. |
| 9,084,591 B2 | 7/2015 | Reglos et al. |
| 9,113,854 B2 | 8/2015 | Ellman |
| 9,119,730 B2 | 9/2015 | Glerum et al. |
| 9,125,757 B2 | 9/2015 | Weiman |
| 9,132,021 B2 | 9/2015 | Mermuys et al. |
| 9,138,217 B2 | 9/2015 | Smith et al. |
| 9,138,330 B2 | 9/2015 | Hansell et al. |
| 9,138,331 B2 | 9/2015 | Aferzon |
| 9,149,367 B2 | 10/2015 | Davenport et al. |
| 9,155,628 B2 | 10/2015 | Glerum et al. |
| 9,155,631 B2 | 10/2015 | Seifert et al. |
| 9,161,841 B2 | 10/2015 | Kana et al. |
| 9,179,903 B2 | 11/2015 | Cianfrani et al. |
| 9,179,952 B2 | 11/2015 | Biedermann et al. |
| 9,186,193 B2 | 11/2015 | Kleiner et al. |
| 9,186,258 B2 | 11/2015 | Davenport et al. |
| 9,192,482 B1 | 11/2015 | Pimenta et al. |
| 9,192,483 B1 | 11/2015 | Radcliffe et al. |
| 9,198,772 B2 | 12/2015 | Weiman |
| 9,204,972 B2 | 12/2015 | Weiman et al. |
| 9,204,974 B2 | 12/2015 | Glerum et al. |
| 9,211,194 B2 | 12/2015 | Bagga et al. |
| 9,211,196 B2 | 12/2015 | Glerum et al. |
| 9,216,095 B2 | 12/2015 | Glerum et al. |
| 9,226,836 B2 | 1/2016 | Glerum |
| 9,233,007 B2 | 1/2016 | Sungarian et al. |
| 9,233,009 B2 | 1/2016 | Gray et al. |
| 9,233,010 B2 | 1/2016 | Thalgott et al. |
| 9,259,327 B2 | 2/2016 | Niemiec et al. |
| 9,271,846 B2 | 3/2016 | Lim et al. |
| 9,308,099 B2 | 4/2016 | Triplett et al. |
| 9,320,610 B2 | 4/2016 | Alheidt et al. |
| 9,351,845 B1 | 5/2016 | Pimenta et al. |
| 9,351,848 B2 | 5/2016 | Glerum et al. |
| 9,357,909 B2 | 6/2016 | Perez-Cruet et al. |
| 9,358,126 B2 | 6/2016 | Glerum et al. |
| 9,358,127 B2 | 6/2016 | Duffield et al. |
| 9,358,128 B2 | 6/2016 | Glerum et al. |
| 9,358,129 B2 | 6/2016 | Weiman |
| 9,364,343 B2 | 6/2016 | Duffield et al. |
| 9,370,434 B2 | 6/2016 | Weiman |
| 9,370,435 B2 | 6/2016 | Walkenhorst et al. |
| 9,381,008 B2 | 7/2016 | Thornburg |
| 9,386,916 B2 | 7/2016 | Predick et al. |
| 9,387,092 B2 | 7/2016 | Mermuys et al. |
| 9,402,673 B2 | 8/2016 | Cormier et al. |
| 9,402,739 B2 | 8/2016 | Weiman et al. |
| 9,408,596 B2 | 8/2016 | Blain |
| 9,408,708 B2 | 8/2016 | Greenhalgh |
| 9,414,828 B2 | 8/2016 | Abidin et al. |
| 9,414,934 B2 | 8/2016 | Cain |
| 9,414,937 B2 | 8/2016 | Carlson et al. |
| 9,421,110 B2 | 8/2016 | Masson et al. |
| 9,427,331 B2 | 8/2016 | Amin |
| 9,445,919 B2 | 9/2016 | Palmatier et al. |
| 9,452,063 B2 | 9/2016 | Glerum et al. |
| 9,456,903 B2 | 10/2016 | Glerum et al. |
| 9,456,906 B2 | 10/2016 | Gray et al. |
| 9,468,405 B2 | 10/2016 | Miles et al. |
| 9,474,622 B2 | 10/2016 | McLaughlin et al. |
| 9,474,625 B2 | 10/2016 | Weiman |
| 9,480,573 B2 | 11/2016 | Perloff et al. |
| 9,480,576 B2 | 11/2016 | Pepper et al. |
| 9,480,579 B2 | 11/2016 | Davenport et al. |
| 9,486,133 B2 | 11/2016 | Lee et al. |
| 9,486,325 B2 | 11/2016 | Davenport et al. |
| 9,486,327 B2 | 11/2016 | Martynova et al. |
| 9,486,328 B2 | 11/2016 | Jimenez et al. |
| 9,492,287 B2 | 11/2016 | Glerum et al. |
| 9,492,288 B2 | 11/2016 | Wagner et al. |
| 9,492,289 B2 | 11/2016 | Davenport et al. |
| 9,498,349 B2 | 11/2016 | Patterson et al. |

(56) References Cited

U.S. PATENT DOCUMENTS

| | | |
|---|---|---|
| 9,510,954 B2 | 12/2016 | Glerum et al. |
| 9,517,098 B2 | 12/2016 | Anderson |
| 9,522,070 B2 | 12/2016 | Flower et al. |
| 9,526,620 B2 | 12/2016 | Slivka et al. |
| 9,526,625 B2 | 12/2016 | Cain |
| 9,532,821 B2 | 1/2017 | Moskowitz et al. |
| 9,539,103 B2 | 1/2017 | McLaughlin et al. |
| 9,539,108 B2 | 1/2017 | Glerum et al. |
| 9,545,320 B2 | 1/2017 | Padovani et al. |
| 9,549,723 B2 | 1/2017 | Hynes et al. |
| 9,549,824 B2 | 1/2017 | McAfee |
| 9,561,116 B2 | 2/2017 | Weiman et al. |
| 9,566,163 B2 | 2/2017 | Suddaby et al. |
| 9,566,166 B2 | 2/2017 | Parry et al. |
| 9,566,168 B2 | 2/2017 | Glerum et al. |
| 9,572,560 B2 | 2/2017 | Mast et al. |
| 9,572,677 B2 | 2/2017 | Davenport et al. |
| 9,572,681 B2 | 2/2017 | Mathieu et al. |
| 9,579,124 B2 | 2/2017 | Gordon et al. |
| 9,579,139 B2 | 2/2017 | Cormier et al. |
| 9,579,213 B2 | 2/2017 | Bal et al. |
| 9,585,649 B2 | 3/2017 | Blain et al. |
| 9,585,762 B2 | 3/2017 | Suddaby et al. |
| 9,585,766 B2 | 3/2017 | Robinson |
| 9,585,767 B2 | 3/2017 | Robinson |
| 9,592,129 B2 | 3/2017 | Slivka et al. |
| 9,597,195 B2 | 3/2017 | Cain |
| 9,603,643 B2 | 3/2017 | Reed et al. |
| 9,603,713 B2 | 3/2017 | Moskowitz et al. |
| 9,603,717 B2 | 3/2017 | Ibarra et al. |
| 9,615,818 B2 | 4/2017 | Baudouin et al. |
| 9,615,936 B2 | 4/2017 | Duffield et al. |
| 9,622,732 B2 | 4/2017 | Martinelli et al. |
| 9,622,875 B2 | 4/2017 | Moskowitz et al. |
| 9,622,876 B1 | 4/2017 | Greenhalgh et al. |
| 9,629,729 B2 | 4/2017 | Grimberg, Jr. et al. |
| 9,636,097 B2 | 5/2017 | Bass |
| 9,642,720 B2 | 5/2017 | Radcliffe et al. |
| 9,649,198 B2 | 5/2017 | Wolters et al. |
| 9,655,746 B2 | 5/2017 | Seifert |
| 9,655,747 B2 | 5/2017 | Glerum et al. |
| 9,662,224 B2 | 5/2017 | Weiman et al. |
| 9,668,784 B2 | 6/2017 | Brumfield et al. |
| 9,668,876 B2 | 6/2017 | Blain et al. |
| 9,668,879 B2 | 6/2017 | Jimenez et al. |
| 9,675,465 B2 | 6/2017 | Padovani et al. |
| 9,675,467 B2 | 6/2017 | Duffield et al. |
| 9,675,468 B1 | 6/2017 | Jensen |
| 9,693,871 B2 | 7/2017 | Richerme et al. |
| 9,700,428 B2 | 7/2017 | Niemiec et al. |
| 9,707,092 B2 | 7/2017 | Davenport et al. |
| 9,713,536 B2 | 7/2017 | Foley et al. |
| 9,717,601 B2 | 8/2017 | Miller |
| 9,730,684 B2 | 8/2017 | Beale et al. |
| 9,730,806 B2 | 8/2017 | Capote |
| 9,737,288 B2 | 8/2017 | Karpowicz et al. |
| 9,750,617 B2 | 9/2017 | Lim et al. |
| 9,750,618 B1 | 9/2017 | Daffinson et al. |
| 9,757,249 B2 | 9/2017 | Radcliffe et al. |
| 9,763,722 B2 | 9/2017 | Roybal |
| 9,770,343 B2 | 9/2017 | Weiman |
| 9,782,265 B2 | 10/2017 | Weiman et al. |
| 9,788,971 B1 | 10/2017 | Stein |
| 9,795,370 B2 | 10/2017 | O'Connell et al. |
| 9,795,371 B2 | 10/2017 | Miles et al. |
| 9,801,733 B2 | 10/2017 | Wolters et al. |
| 9,801,734 B1 | 10/2017 | Stein et al. |
| 9,808,352 B2 | 11/2017 | Suddaby et al. |
| 9,826,966 B2 | 11/2017 | Mast et al. |
| 9,827,024 B2 | 11/2017 | Cormier et al. |
| 9,827,107 B1 | 11/2017 | Amin |
| 9,833,333 B2 | 12/2017 | Duffield et al. |
| 9,833,336 B2 | 12/2017 | Davenport et al. |
| 9,839,527 B2 | 12/2017 | Robinson |
| 9,839,528 B2 | 12/2017 | Weiman et al. |
| 9,848,993 B2 | 12/2017 | Moskowitz et al. |
| 9,848,996 B2 | 12/2017 | Faulhaber |
| 9,855,151 B2 | 1/2018 | Weiman |
| 9,867,715 B2 | 1/2018 | Mclaughlin et al. |
| 9,872,779 B2 | 1/2018 | Miller et al. |
| 9,889,019 B2 | 2/2018 | Rogers et al. |
| 9,907,671 B2 | 3/2018 | Fessler |
| 9,907,673 B2 | 3/2018 | Weiman et al. |
| 9,918,709 B2 | 3/2018 | Sandhu |
| 9,924,859 B2 | 3/2018 | Lee et al. |
| 9,924,940 B2 | 3/2018 | Moskowitz et al. |
| 9,925,062 B2 | 3/2018 | Glerum et al. |
| 9,925,064 B2 | 3/2018 | Duffield et al. |
| 9,931,223 B2 | 4/2018 | Cain |
| 9,937,053 B2 | 4/2018 | Melkent et al. |
| 9,943,342 B2 | 4/2018 | Tanaka et al. |
| 9,943,418 B2 | 4/2018 | Davenport et al. |
| 9,949,775 B2 | 4/2018 | Reed et al. |
| 9,949,841 B2 | 4/2018 | Glerum et al. |
| 9,956,087 B2 | 5/2018 | Seifert et al. |
| 9,962,202 B2 | 5/2018 | Anderson |
| 9,962,270 B2 | 5/2018 | Alheidt et al. |
| 9,962,271 B2 | 5/2018 | Glerum |
| 9,962,272 B1 | 5/2018 | Daffinson et al. |
| 9,968,461 B2 | 5/2018 | Zappacosta et al. |
| 9,968,462 B2 | 5/2018 | Weiman |
| 9,974,531 B2 | 5/2018 | Miles et al. |
| 9,974,662 B2 | 5/2018 | Hessler et al. |
| 9,974,664 B2 | 5/2018 | Emerick et al. |
| 9,980,825 B2 | 5/2018 | Nichols et al. |
| 9,980,826 B2 | 5/2018 | Martynova et al. |
| 9,987,141 B2 | 6/2018 | Duffield et al. |
| 9,987,143 B2 | 6/2018 | Robinson et al. |
| 9,987,144 B2 | 6/2018 | Seifert et al. |
| 9,987,146 B1 | 6/2018 | Lentner et al. |
| 9,993,239 B2 | 6/2018 | Karpowicz et al. |
| 9,993,350 B2 | 6/2018 | Cain |
| 10,004,607 B2 | 6/2018 | Weiman et al. |
| 10,016,282 B2 | 7/2018 | Seifert et al. |
| 10,016,284 B2 | 7/2018 | Moskowitz et al. |
| 10,022,239 B1 | 7/2018 | Lentner et al. |
| 10,028,842 B2 | 7/2018 | Gray et al. |
| 10,034,765 B2 | 7/2018 | Blain et al. |
| 10,034,769 B2 | 7/2018 | Baynham |
| 10,034,771 B2 | 7/2018 | Capote et al. |
| 10,034,772 B2 | 7/2018 | Glerum et al. |
| 10,034,773 B2 | 7/2018 | McLaughlin et al. |
| 10,039,539 B2 | 8/2018 | Friedrich et al. |
| 10,039,650 B2 | 8/2018 | Lamborne et al. |
| 10,052,214 B2 | 8/2018 | Jimenez et al. |
| 10,058,431 B2 | 8/2018 | Tyber et al. |
| 10,060,469 B2 | 8/2018 | Jimenez et al. |
| 10,070,852 B2 | 9/2018 | Mast et al. |
| 10,076,320 B2 | 9/2018 | Mast et al. |
| 10,076,423 B2 | 9/2018 | Miller et al. |
| 10,080,666 B2 | 9/2018 | Suddaby et al. |
| 10,080,669 B2 | 9/2018 | Davenport et al. |
| 10,085,846 B2 | 10/2018 | Grotz |
| 10,085,849 B2 | 10/2018 | Weiman et al. |
| 10,092,417 B2 | 10/2018 | Weiman et al. |
| 10,098,758 B2 | 10/2018 | Matthews et al. |
| 10,098,759 B2 | 10/2018 | Weiman |
| 10,111,755 B2 | 10/2018 | Foley et al. |
| 10,111,758 B2 | 10/2018 | Robinson |
| 10,117,754 B2 | 11/2018 | Davenport et al. |
| 10,117,755 B2 | 11/2018 | Emerick et al. |
| 10,137,002 B2 | 11/2018 | Padovani et al. |
| 10,137,006 B2 | 11/2018 | Dewey et al. |
| 10,137,007 B2 | 11/2018 | Dewey et al. |
| 10,137,009 B2 | 11/2018 | Weiman et al. |
| 10,149,671 B2 | 12/2018 | Predick et al. |
| 10,149,710 B2 | 12/2018 | Tanaka et al. |
| 10,154,781 B2 | 12/2018 | Weiman |
| 10,154,912 B2 | 12/2018 | Glerum |
| 10,154,914 B2 | 12/2018 | Robinson |
| 10,159,584 B2 | 12/2018 | Carnes et al. |
| 10,166,117 B1 | 1/2019 | Daffinson et al. |
| 10,172,515 B2 | 1/2019 | Lee et al. |
| 10,172,652 B2 | 1/2019 | Woolley et al. |

(56) References Cited

U.S. PATENT DOCUMENTS

| | | |
|---|---|---|
| 10,178,987 B2 | 1/2019 | Predick et al. |
| 10,179,053 B2 | 1/2019 | Zappacosta et al. |
| 10,182,922 B2 | 1/2019 | Nichols et al. |
| 10,188,527 B2 | 1/2019 | Rogers et al. |
| 10,195,050 B2 | 2/2019 | Palmatier et al. |
| 10,201,431 B2 | 2/2019 | Slater et al. |
| 10,213,192 B2 | 2/2019 | Capote |
| 10,213,193 B2 | 2/2019 | Karpowicz et al. |
| 10,219,798 B2 | 3/2019 | Capote |
| 10,219,913 B2 | 3/2019 | Matthews et al. |
| 10,219,914 B2 | 3/2019 | Faulhaber |
| 10,219,915 B1 | 3/2019 | Stein |
| 10,226,356 B2 | 3/2019 | Grotz |
| 10,226,359 B2 | 3/2019 | Glerum et al. |
| 10,238,375 B2 | 3/2019 | O'Connell et al. |
| 10,238,383 B2 | 3/2019 | Moskowitz et al. |
| 10,238,503 B2 | 3/2019 | Branch et al. |
| 10,245,015 B2 | 4/2019 | Predick et al. |
| 10,251,643 B2 | 4/2019 | Moskowitz et al. |
| 10,265,191 B2 | 4/2019 | Lim et al. |
| 10,278,686 B2 | 5/2019 | Baudouin et al. |
| 10,278,786 B2 | 5/2019 | Friedrich et al. |
| 10,278,830 B1 | 5/2019 | Walker et al. |
| 10,278,831 B2 | 5/2019 | Sandul |
| 10,278,832 B2 | 5/2019 | Nichols et al. |
| 10,285,680 B2 | 5/2019 | Friedrich et al. |
| 10,285,819 B2 | 5/2019 | Greenhalgh |
| 10,285,824 B2 | 5/2019 | Robinson |
| 10,292,828 B2 | 5/2019 | Greenhalgh |
| 10,299,777 B2 | 5/2019 | Mast et al. |
| 10,299,934 B2 | 5/2019 | Seifert et al. |
| 10,299,937 B2 | 5/2019 | McAfee |
| 10,307,268 B2 | 6/2019 | Moskowitz et al. |
| 10,314,622 B2 | 6/2019 | Brumfield et al. |
| 10,314,719 B2 | 6/2019 | Hessler et al. |
| 10,322,007 B2 | 6/2019 | Masson et al. |
| 10,322,009 B2 | 6/2019 | Aghayev et al. |
| 10,327,909 B2 | 6/2019 | Baynham |
| 10,327,912 B1 | 6/2019 | Suddaby |
| 10,327,917 B2 | 6/2019 | Glerum et al. |
| 10,342,675 B2 | 7/2019 | Alheidt |
| 10,350,085 B2 | 7/2019 | Glerum et al. |
| 10,357,233 B2 | 7/2019 | Miles et al. |
| 10,363,142 B2 | 7/2019 | McClintock et al. |
| 10,363,144 B2 | 7/2019 | Overes et al. |
| 10,369,004 B2 | 8/2019 | Faulhaber |
| 10,369,008 B2 | 8/2019 | Jimenez et al. |
| 10,369,010 B2 | 8/2019 | Robinson et al. |
| 10,369,012 B2 | 8/2019 | Fessler |
| 10,376,377 B2 | 8/2019 | Seifert et al. |
| 10,390,962 B2 | 8/2019 | Weiman |
| 10,390,964 B2 | 8/2019 | Faulhaber |
| 10,398,563 B2 | 9/2019 | Engstrom |
| 10,398,566 B2 | 9/2019 | Olmos et al. |
| 10,413,419 B2 | 9/2019 | Thibodeau |
| 10,413,422 B2 | 9/2019 | Flower et al. |
| 10,413,423 B2 | 9/2019 | Overes et al. |
| 10,426,450 B2 | 10/2019 | Vogel et al. |
| 10,426,633 B2 | 10/2019 | Moskowitz et al. |
| 10,426,634 B1 | 10/2019 | Al-Jazaeri et al. |
| 10,441,430 B2 | 10/2019 | Ludwig et al. |
| 10,449,056 B2 | 10/2019 | Cain |
| 10,456,122 B2 | 10/2019 | Koltz et al. |
| 10,470,894 B2 | 11/2019 | Foley et al. |
| 10,478,319 B2 | 11/2019 | Moskowitz et al. |
| 10,492,912 B2 | 12/2019 | Gregersen et al. |
| 10,492,922 B2 | 12/2019 | Mathieu et al. |
| 10,492,924 B2 | 12/2019 | Stein et al. |
| 10,500,064 B2 | 12/2019 | Robinson |
| 10,512,550 B2 | 12/2019 | Bechtel et al. |
| 10,517,645 B2 | 12/2019 | van der Pol |
| 10,524,924 B2 | 1/2020 | Davenport et al. |
| 10,531,903 B2 | 1/2020 | Daly et al. |
| 10,537,436 B2 | 1/2020 | Maguire et al. |
| 10,537,438 B2 | 1/2020 | Martynova et al. |
| 10,555,729 B1 | 2/2020 | Cole et al. |
| 10,561,411 B1 | 2/2020 | Cole et al. |
| 10,575,889 B2 | 3/2020 | Roybal |
| 10,575,960 B2 | 3/2020 | Duffield et al. |
| 10,582,959 B2 | 3/2020 | Langer et al. |
| 10,583,015 B2 | 3/2020 | Olmos et al. |
| 10,603,078 B2 | 3/2020 | Simpson et al. |
| 10,610,376 B2 | 4/2020 | Kuyler et al. |
| 10,624,757 B2 | 4/2020 | Bost et al. |
| 10,624,758 B2 | 4/2020 | Slivka et al. |
| 10,624,761 B2 | 4/2020 | Davenport et al. |
| 10,639,163 B2 | 5/2020 | Tyber et al. |
| 10,639,166 B2 | 5/2020 | Weiman et al. |
| 10,653,458 B2 | 5/2020 | Tanaka et al. |
| 10,667,925 B2 | 6/2020 | Emerick et al. |
| 10,667,927 B2 | 6/2020 | Lamborne et al. |
| 10,675,157 B2 | 6/2020 | Zakelj et al. |
| 10,682,241 B2 | 6/2020 | Glerum et al. |
| 10,687,963 B2 | 6/2020 | Jimenez et al. |
| 10,702,393 B2 | 7/2020 | Davenport et al. |
| 10,709,569 B2 | 7/2020 | McLaughlin et al. |
| 10,709,571 B2 | 7/2020 | Iott et al. |
| 10,709,572 B2 | 7/2020 | Daffinson et al. |
| 10,709,575 B2 | 7/2020 | Robinson |
| 10,722,377 B2 | 7/2020 | Glerum et al. |
| 10,722,379 B2 | 7/2020 | McLaughlin et al. |
| 10,729,561 B2 | 8/2020 | Glerum |
| 10,743,858 B1 | 8/2020 | Cole et al. |
| 10,744,002 B2 | 8/2020 | Glerum et al. |
| 10,758,366 B2 | 9/2020 | Daffinson et al. |
| 10,758,367 B2 | 9/2020 | Weiman et al. |
| 10,758,369 B2 | 9/2020 | Rogers et al. |
| 10,765,528 B2 | 9/2020 | Weiman et al. |
| 10,772,737 B2 | 9/2020 | Gray et al. |
| 10,779,955 B2 | 9/2020 | Kuyler et al. |
| 10,779,957 B2 | 9/2020 | Weiman et al. |
| 10,786,364 B2 | 9/2020 | Davenport et al. |
| 10,786,369 B2 | 9/2020 | Carnes et al. |
| 10,799,368 B2 | 10/2020 | Glerum et al. |
| 10,835,387 B2 | 11/2020 | Weiman et al. |
| 10,842,640 B2 | 11/2020 | Weiman et al. |
| 10,842,644 B2 | 11/2020 | Weiman et al. |
| 10,856,997 B2 | 12/2020 | Cowan et al. |
| 10,869,769 B2 | 12/2020 | Eisen et al. |
| 10,874,447 B2 | 12/2020 | Tanaka et al. |
| 10,874,523 B2 | 12/2020 | Weiman et al. |
| 10,874,524 B2 | 12/2020 | Bjork |
| 10,925,656 B2 | 2/2021 | Cole et al. |
| 10,959,855 B2 | 3/2021 | Miller et al. |
| 11,058,469 B2 | 7/2021 | Mahajan et al. |
| 11,147,680 B2 | 10/2021 | Tyber et al. |
| 11,179,234 B2 | 11/2021 | Dacosta et al. |
| 2002/0045943 A1 | 4/2002 | Uk |
| 2002/0045945 A1 | 4/2002 | Liu et al. |
| 2002/0116066 A1 | 8/2002 | Chauvin et al. |
| 2002/0128713 A1 | 9/2002 | Ferree |
| 2002/0151976 A1 | 10/2002 | Foley et al. |
| 2003/0050701 A1 | 3/2003 | Michelson |
| 2003/0130739 A1 | 7/2003 | Gerbec et al. |
| 2004/0172134 A1 | 9/2004 | Berry |
| 2004/0186570 A1 | 9/2004 | Rapp |
| 2004/0193158 A1 | 9/2004 | Lim et al. |
| 2004/0249461 A1 | 12/2004 | Ferree |
| 2004/0254643 A1 | 12/2004 | Jackson |
| 2004/0254644 A1 | 12/2004 | Taylor |
| 2005/0015149 A1 | 1/2005 | Michelson |
| 2005/0033429 A1 | 2/2005 | Kuo |
| 2005/0033439 A1 | 2/2005 | Gordon et al. |
| 2006/0122701 A1 | 6/2006 | Kiester |
| 2006/0129244 A1* | 6/2006 | Ensign ................. A61F 2/4455 623/17.16 |
| 2007/0218750 A1 | 9/2007 | Corrao et al. |
| 2007/0270859 A1 | 11/2007 | Companioni et al. |
| 2008/0132959 A1 | 6/2008 | Mikkonen et al. |
| 2009/0024158 A1 | 1/2009 | Viker |
| 2009/0292361 A1 | 11/2009 | Lopez |
| 2010/0082109 A1 | 4/2010 | Greenhalgh et al. |
| 2010/0191336 A1 | 7/2010 | Greenhalgh |
| 2010/0211176 A1 | 8/2010 | Greenhalgh |

(56) References Cited

U.S. PATENT DOCUMENTS

| | | |
|---|---|---|
| 2011/0118843 A1 | 5/2011 | Mathieu et al. |
| 2011/0130838 A1 | 6/2011 | Morgenstern Lopez |
| 2011/0153020 A1* | 6/2011 | Abdelgany ............ A61F 2/4465 623/17.16 |
| 2011/0218572 A1 | 9/2011 | Lechmann et al. |
| 2012/0095515 A1 | 4/2012 | Hamilton |
| 2012/0101581 A1 | 4/2012 | Mathieu et al. |
| 2012/0109142 A1 | 5/2012 | Dayan |
| 2012/0109309 A1 | 5/2012 | Mathieu et al. |
| 2012/0109310 A1 | 5/2012 | Mathieu et al. |
| 2012/0109312 A1 | 5/2012 | Mathieu et al. |
| 2012/0109313 A1 | 5/2012 | Mathieu et al. |
| 2012/0123546 A1 | 5/2012 | Medina |
| 2012/0150237 A1 | 6/2012 | Combrowski |
| 2012/0197401 A1 | 8/2012 | Duncan et al. |
| 2012/0209385 A1 | 8/2012 | Aferzon |
| 2012/0215316 A1 | 8/2012 | Mohr et al. |
| 2013/0103153 A1* | 4/2013 | Blackwell ............ A61F 2/4611 623/17.16 |
| 2013/0190876 A1 | 7/2013 | Drochner et al. |
| 2013/0226191 A1 | 8/2013 | Thoren et al. |
| 2013/0231747 A1 | 9/2013 | Olmos et al. |
| 2013/0304136 A1 | 11/2013 | Gourlaouen-Preissler et al. |
| 2013/0317312 A1 | 11/2013 | Eastlack et al. |
| 2014/0107790 A1 | 4/2014 | Combrowski |
| 2014/0114420 A1 | 4/2014 | Robinson |
| 2014/0163682 A1 | 6/2014 | Iott et al. |
| 2014/0180419 A1 | 6/2014 | Dmuschewsky |
| 2014/0194992 A1 | 7/2014 | Medina |
| 2014/0277500 A1* | 9/2014 | Logan ............ A61F 2/447 623/17.16 |
| 2014/0303674 A1 | 10/2014 | Sasing |
| 2015/0223945 A1 | 8/2015 | Weiman et al. |
| 2015/0230931 A1 | 8/2015 | Greenhalgh |
| 2015/0238236 A1 | 8/2015 | Sasing |
| 2016/0008924 A1 | 1/2016 | Canourgues et al. |
| 2016/0022434 A1 | 1/2016 | Robinson |
| 2016/0081681 A1 | 3/2016 | Waugh et al. |
| 2016/0089247 A1 | 3/2016 | Nichols et al. |
| 2016/0095710 A1 | 4/2016 | Juszczyk et al. |
| 2016/0242930 A1 | 8/2016 | Duffield et al. |
| 2016/0256291 A1 | 9/2016 | Miller |
| 2016/0278830 A1 | 9/2016 | Arrington |
| 2016/0296340 A1 | 10/2016 | Gordon et al. |
| 2016/0310291 A1 | 10/2016 | Greenhalgh |
| 2016/0345952 A1 | 12/2016 | Kucharzyk et al. |
| 2016/0367377 A1 | 12/2016 | Faulhaber |
| 2017/0010025 A1 | 1/2017 | Mayershofer |
| 2017/0029635 A1 | 2/2017 | Doll et al. |
| 2017/0035406 A1 | 2/2017 | Abidin et al. |
| 2017/0049651 A1 | 2/2017 | Lim et al. |
| 2017/0049653 A1 | 2/2017 | Lim et al. |
| 2017/0095345 A1 | 4/2017 | Davenport et al. |
| 2017/0100255 A1 | 4/2017 | Hleihil et al. |
| 2017/0100257 A1 | 4/2017 | Weiman et al. |
| 2017/0105844 A1 | 4/2017 | Kuyler et al. |
| 2017/0151065 A1 | 6/2017 | Warren et al. |
| 2017/0156882 A1 | 6/2017 | Rathbun et al. |
| 2017/0156884 A1 | 6/2017 | Rathbun et al. |
| 2017/0189204 A1 | 7/2017 | Riemhofer et al. |
| 2017/0202678 A1 | 7/2017 | Duffield et al. |
| 2017/0215856 A1 | 8/2017 | Martinelli et al. |
| 2017/0224502 A1 | 8/2017 | Wolters et al. |
| 2017/0231675 A1 | 8/2017 | Combrowski |
| 2017/0246006 A1 | 8/2017 | Carnes et al. |
| 2017/0290677 A1 | 10/2017 | Olmos et al. |
| 2017/0296352 A1* | 10/2017 | Richerme ............ A61F 2/4425 |
| 2017/0367842 A1 | 12/2017 | Predick et al. |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0030362 A1 | 2/2018 | Kosler et al. |
| 2018/0031810 A1 | 2/2018 | Hsu et al. |
| 2018/0036136 A1 | 2/2018 | Duffield et al. |
| 2018/0036138 A1 | 2/2018 | Robinson |
| 2018/0116891 A1 | 5/2018 | Beale et al. |
| 2018/0193164 A1 | 7/2018 | Shoshtaev |
| 2018/0206999 A1 | 7/2018 | Suddaby |
| 2018/0256356 A1 | 9/2018 | Robinson et al. |
| 2018/0256359 A1 | 9/2018 | Greenhalgh |
| 2018/0256360 A1 | 9/2018 | Cain |
| 2018/0256362 A1 | 9/2018 | Slivka et al. |
| 2018/0263784 A1 | 9/2018 | Bechtel et al. |
| 2018/0280142 A1 | 10/2018 | Schultz et al. |
| 2018/0303473 A1 | 10/2018 | Spann et al. |
| 2018/0303621 A1 | 10/2018 | Brotman et al. |
| 2018/0303625 A1 | 10/2018 | Alheidt et al. |
| 2018/0311048 A1 | 11/2018 | Glerum et al. |
| 2018/0318101 A1 | 11/2018 | Engstrom |
| 2018/0318102 A1 | 11/2018 | Seifert et al. |
| 2018/0338838 A1 | 11/2018 | Cryder et al. |
| 2018/0338841 A1 | 11/2018 | Miller et al. |
| 2018/0344307 A1 | 12/2018 | Hynes et al. |
| 2018/0360616 A1 | 12/2018 | Luu |
| 2019/0000640 A1 | 1/2019 | Weiman |
| 2019/0000702 A1 | 1/2019 | Lim et al. |
| 2019/0000707 A1 | 1/2019 | Lim et al. |
| 2019/0020121 A1 | 1/2019 | Paulotto et al. |
| 2019/0021716 A1 | 1/2019 | Waugh et al. |
| 2019/0021873 A1 | 1/2019 | Dmuschewsky |
| 2019/0046329 A1 | 2/2019 | Padovani et al. |
| 2019/0046381 A1 | 2/2019 | Lim et al. |
| 2019/0046383 A1 | 2/2019 | Lim et al. |
| 2019/0060083 A1 | 2/2019 | Weiman et al. |
| 2019/0082949 A1 | 3/2019 | Weiman |
| 2019/0083081 A1 | 3/2019 | Ortiz et al. |
| 2019/0091033 A1 | 3/2019 | Dewey et al. |
| 2019/0105175 A1 | 4/2019 | Zappacosta et al. |
| 2019/0125328 A1 | 5/2019 | Blain |
| 2019/0133434 A1 | 5/2019 | Lee et al. |
| 2019/0133645 A1 | 5/2019 | Gordon et al. |
| 2019/0133780 A1 | 5/2019 | Matthews et al. |
| 2019/0133784 A1 | 5/2019 | Gunn et al. |
| 2019/0133788 A1 | 5/2019 | Weiman et al. |
| 2019/0142480 A1 | 5/2019 | Woolley et al. |
| 2019/0151115 A1 | 5/2019 | Nichols et al. |
| 2019/0183656 A1 | 6/2019 | Stein |
| 2019/0201209 A1 | 7/2019 | Branch et al. |
| 2019/0201210 A1 | 7/2019 | Besaw et al. |
| 2019/0209155 A1 | 7/2019 | Mast et al. |
| 2019/0216453 A1 | 7/2019 | Predick et al. |
| 2019/0231552 A1 | 8/2019 | Sandul |
| 2019/0240039 A1 | 8/2019 | Walker et al. |
| 2019/0240043 A1 | 8/2019 | Greenhalgh |
| 2019/0247098 A1 | 8/2019 | Brumfield et al. |
| 2019/0254650 A1 | 8/2019 | Martinelli et al. |
| 2019/0254838 A1 | 8/2019 | Miller et al. |
| 2019/0254839 A1 | 8/2019 | Nichols et al. |
| 2019/0262139 A1 | 8/2019 | Wolters |
| 2019/0269521 A1 | 9/2019 | Shoshtaev |
| 2019/0274670 A1 | 9/2019 | O'Connell et al. |
| 2019/0274671 A1 | 9/2019 | Lauf et al. |
| 2019/0274836 A1 | 9/2019 | Eisen et al. |
| 2019/0282373 A1 | 9/2019 | Alheidt |
| 2019/0290446 A1 | 9/2019 | Masson et al. |
| 2019/0290447 A1 | 9/2019 | Stein |
| 2019/0298416 A1 | 10/2019 | Rezach |
| 2019/0298524 A1 | 10/2019 | Lauf et al. |
| 2019/0298540 A1 | 10/2019 | Aghayev et al. |
| 2019/0321022 A1 | 10/2019 | Karpowicz et al. |
| 2019/0321190 A1 | 10/2019 | Wagner et al. |
| 2019/0328540 A1 | 10/2019 | Seifert et al. |
| 2019/0336301 A1 | 11/2019 | Engstrom |
| 2019/0336304 A1 | 11/2019 | Burkhardt et al. |
| 2019/0350573 A1 | 11/2019 | Vogel et al. |
| 2019/0358049 A1 | 11/2019 | Faulhaber |
| 2019/0358050 A1 | 11/2019 | Fessler |
| 2019/0358051 A1 | 11/2019 | Flower et al. |
| 2019/0388232 A1 | 12/2019 | Purcell et al. |
| 2020/0008951 A1 | 1/2020 | McClintock et al. |
| 2020/0030114 A1 | 1/2020 | Cain |
| 2020/0030116 A1 | 1/2020 | Jimenez et al. |
| 2020/0038200 A1 | 2/2020 | Foley et al. |
| 2020/0054461 A1 | 2/2020 | Marrocco et al. |

(56) References Cited

U.S. PATENT DOCUMENTS

| | | |
|---|---|---|
| 2020/0060844 A1 | 2/2020 | Mathieu et al. |
| 2020/0078190 A1 | 3/2020 | Rogers et al. |
| 2020/0093526 A1 | 3/2020 | Daly et al. |
| 2020/0093607 A1 | 3/2020 | Davenport et al. |
| 2020/0093609 A1 | 3/2020 | Shoshtaev |
| 2020/0100904 A1 | 4/2020 | Stein et al. |
| 2020/0129306 A1 | 4/2020 | Miller et al. |
| 2020/0129307 A1 | 4/2020 | Hunziker et al. |
| 2020/0138591 A1 | 5/2020 | Moskowitz et al. |
| 2020/0138593 A1 | 5/2020 | Martynova et al. |
| 2020/0146840 A1 | 5/2020 | Black et al. |
| 2020/0179120 A1 | 6/2020 | Bielenstein et al. |
| 2020/0205993 A1 | 7/2020 | Davenport et al. |
| 2020/0222202 A1 | 7/2020 | Kuyler et al. |
| 2020/0229944 A1 | 7/2020 | Suh et al. |
| 2020/0246159 A1 | 8/2020 | Suh et al. |
| 2020/0246162 A1 | 8/2020 | Schultz et al. |
| 2020/0261242 A1 | 8/2020 | Bost et al. |
| 2020/0268524 A1 | 8/2020 | Glerum et al. |
| 2020/0276028 A1 | 9/2020 | Blain et al. |
| 2020/0289287 A1 | 9/2020 | Emerick et al. |
| 2020/0297507 A1 | 9/2020 | Iott et al. |
| 2020/0330239 A1 | 10/2020 | Davenport et al. |
| 2020/0330245 A1 | 10/2020 | Glerum |
| 2020/0345511 A1 | 11/2020 | Daffinson et al. |
| 2020/0352731 A1 | 11/2020 | Berry |
| 2020/0352738 A1 | 11/2020 | Berry |
| 2020/0360153 A1 | 11/2020 | Weiman et al. |
| 2020/0375753 A1 | 12/2020 | McLaughlin et al. |
| 2020/0375755 A1 | 12/2020 | Cain |
| 2020/0383797 A1 | 12/2020 | Predick et al. |
| 2020/0383799 A1 | 12/2020 | Cain |
| 2020/0390565 A1 | 12/2020 | Jimenez et al. |
| 2020/0397593 A1 | 12/2020 | Davenport et al. |
| 2020/0405498 A1 | 12/2020 | Gray et al. |
| 2020/0405499 A1 | 12/2020 | Gerbec et al. |
| 2020/0405500 A1 | 12/2020 | Cain |
| 2021/0137701 A1 | 5/2021 | Miller et al. |
| 2021/0154811 A1 | 5/2021 | Spreiter et al. |
| 2021/0315707 A1* | 10/2021 | Keller ............... A61F 2/447 |
| 2022/0015919 A1* | 1/2022 | Reah ............... A61F 2/447 |
| 2022/0133498 A1* | 5/2022 | Josse ............... A61F 2/30771 623/17.11 |

FOREIGN PATENT DOCUMENTS

| | | |
|---|---|---|
| EP | 0 880 950 A1 | 12/1998 |
| EP | 0 857 042 B1 | 11/2001 |
| EP | 1 442 732 A1 | 8/2004 |
| EP | 1 124 512 B1 | 9/2004 |
| EP | 1 107 711 B1 | 10/2004 |
| EP | 1 506 753 A1 | 2/2005 |
| EP | 1 459 711 B1 | 7/2007 |
| FR | 2781998 A1 | 2/2000 |
| FR | 3082115 A1 | 12/2019 |
| GB | 2 377 387 A | 1/2003 |
| WO | 92/14423 A1 | 9/1992 |
| WO | 97/ 00054 A1 | 1/1997 |
| WO | 99/ 26562 A1 | 6/1999 |
| WO | 99/66867 A1 | 12/1999 |
| WO | 00/12033 A1 | 3/2000 |
| WO | 00/25706 A1 | 5/2000 |
| WO | 00/ 49977 A1 | 8/2000 |
| WO | 02/19952 A1 | 3/2002 |
| WO | 03/105673 A2 | 12/2003 |
| WO | 2014/133755 A1 | 9/2014 |
| WO | 2017/168208 A1 | 10/2017 |
| WO | 2018049227 A1 | 3/2018 |

OTHER PUBLICATIONS

International Search Report and Written Opinion for Application No. PCT/US2019/019060, dated Jun. 5, 2019.
International Search Report and Written Opinion, PCT/IB2020/000932, dated Jul. 29, 2021.
International Search Report and Written Opinion, PCT/IB2020/000942, dated Aug. 10, 2021.
European Search Report, EP19756905, dated Oct. 18, 2021.

* cited by examiner

INTERBODY IMPLANT WITH ADJUSTING SHIMS

CROSS-REFERENCE TO RELATED APPLICATIONS

This application incorporates by reference U.S. patent application Ser. No. 17/515,735 titled INTERBODY IMPLANT WITH ADJUSTING SHIMS, and filed Nov. 1, 2021; U.S. patent application Ser. No. 17/356,950, titled EXPANDABLE INTERBODY IMPLANT; U.S. application Ser. No. 17/307,578, titled EXTERNALLY DRIVEN EXPANDABLE INTERBODY AND RELATED METHODS, and filed May 5, 2021; U.S. Pat. No. 11,096,796, titled Interbody spinal implant having a roughened surface topography on one or more internal surfaces, and filed on Mar. 4, 2013; and U.S. Pat. No. 10,821,000, titled Titanium implant surfaces free from alpha case and with enhanced osteoinduction, and filed Jun. 29, 2017. The entire contents of each is incorporated herein by reference in its entirety.

FIELD

The present technology is generally related to an expandable interbody implant for use in a medical procedure related to the spine. In some embodiments, disclosed implants may be used in an anterior cervical discectomy and fusion (ACDF) procedure although other uses in other areas of the spine or between two bones or bone portions are also contemplated.

BACKGROUND

Mechanically operated interbody implants may be used to align and/or realign a patient's spine during a medical procedure and/or for purposes of fusion, degenerative tissue and/or trauma/repair procedures. Conventional implants designed for the Thoracic and Lumbar region of the spine often include top and bottom endplates and a mechanical means to separate the top and bottom endplates. The mechanical mechanisms to separate the top and bottom endplates are often cumbersome and require a large footprint that is often unsuitable, for example, for ACDF type surgeries of the cervical portion of the spine. Additionally, these mechanical mechanisms may reduce available space in the interior of the implant which in turn may reduce the applicable volume for a fusion process.

SUMMARY

The techniques of this disclosure generally relate to an expandable interbody implant including a superior endplate and an inferior endplate hingedly coupled or combined together. The implant may include at least one shim for adjusting an expansion and/or lordosis or kyphosis of the implant.

In one aspect, the present disclosure is directed to an expandable implant movable between a collapsed position and an expanded position. The implant may include a superior endplate including a first track on an interior surface thereof and an inferior endplate including a second track on an interior surface thereof, for example. The implant may include a first shim having a superior bearing surface for supporting the superior endplate and an inferior bearing surface for supporting the inferior endplate, for example. In a collapsed position the first track may be mated with the second track, and in an expanded position the first shim may define a spacing and angle of inclination between the superior endplate and the inferior endplate, for example.

In another aspect, the present disclosure is directed to an expandable implant movable between a collapsed position and an expanded position, for example. The implant may include a superior endplate including a first track and a second track disposed on an interior surface thereof and an inferior endplate including a third track and a fourth track disposed on an interior surface thereof, for example. Various embodiments may include a first shim having a superior bearing surface for supporting the superior endplate and an inferior bearing surface for supporting the inferior endplate, and a second shim having a superior bearing surface for supporting the superior endplate and an inferior bearing surface for supporting the inferior endplate, for example. In various embodiments, in a collapsed position the first track is mated with the third track and the second track is mated with the fourth track. In various embodiments, in an expanded position the first shim is disposed within the first track and third track and the second shim is disposed within the second track and fourth track, for example. In some embodiments, the first and second shims define a spacing and an angle of inclination between the superior endplate and the inferior endplate, for example.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 24 is a reference drawing showing the human spine of which various disclosed implant embodiments may be installed in.

DETAILED DESCRIPTION

Figure 1:
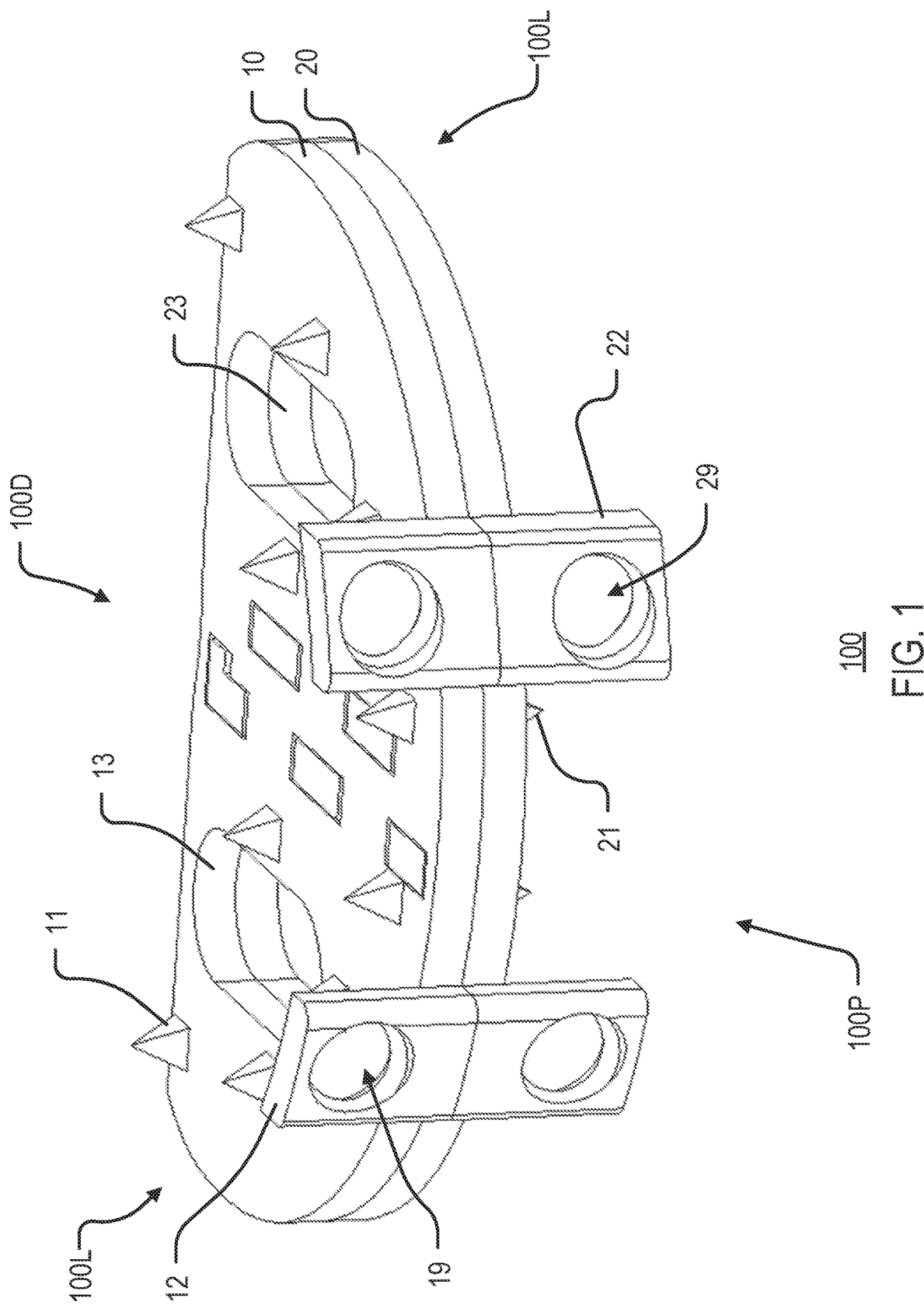
FIG. 1 is a perspective view of an expandable implant in a collapsed position.

Embodiments of the present disclosure relate generally, for example, to spinal stabilization systems, and more particularly, to surgical instruments for use with spinal stabilization systems. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise.

Referring to FIGS. 1-23 generally, various spinal implants 100 are disclosed. The components of spinal implant 100 can be fabricated from biologically acceptable materials suitable for medical applications, including metals, synthetic polymers, ceramics and bone material and/or their composites. For example, the components, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

In various embodiments, components may be coated with a ceramic, titanium, and/or other biocompatible material to provide surface texturing at (a) the macro scale, (b) the micro scale, and/or (c) the nano scale, for example. Similarly, components may undergo a subtractive manufacturing process providing for surface texturing configured to facilitate osseointegration and cellular attachment and osteoblast maturation. Example surface texturing of additive and subtractive manufacturing processes may comprise (a) macro-scale structural features having a maximum peak-to-valley height of about 40 microns to about 500 microns, (b) micro-scale structural features having a maximum peak-to-valley height of about 2 microns to about 40 microns, and/or (c) nano-scale structural features having a maximum peak-to-valley height of about 0.05 microns to about 5 microns. In various embodiments, the three types of structural features may be overlapping with one another, for example. Additionally, such surface texturing may be applied to any surface, e.g., both external exposed facing surfaces of components and internal non exposed surfaces of components. Further discussion regarding relevant surface texturing and coatings is described in, for example, U.S. Pat. No. 11,096, 796, titled Interbody spinal implant having a roughened surface topography on one or more internal surfaces, and filed on Mar. 4, 2013—the entire disclosure of which is incorporated herein by reference in its entirety. Accordingly, it shall be understand that any of the described coating and texturing processes of U.S. Pat. No. 11,096,796, may be applied to any component of the various embodiments disclosed herein, e.g., the exposed surfaces and internal surfaces of endplates. Another example technique for manufacturing an orthopedic implant having surfaces with osteoinducting roughness features including micro-scale structures and nano-scale structures is disclosed in U.S. Pat. No. 10,821,000, the entire contents of which are incorporated herein by reference. Additionally, an example of a commercially available product may be the Adaptix™ Interbody System sold by Medtronic Spine and comprising a titanium cage made with Titan nanoLOCK™.

Figure 2:
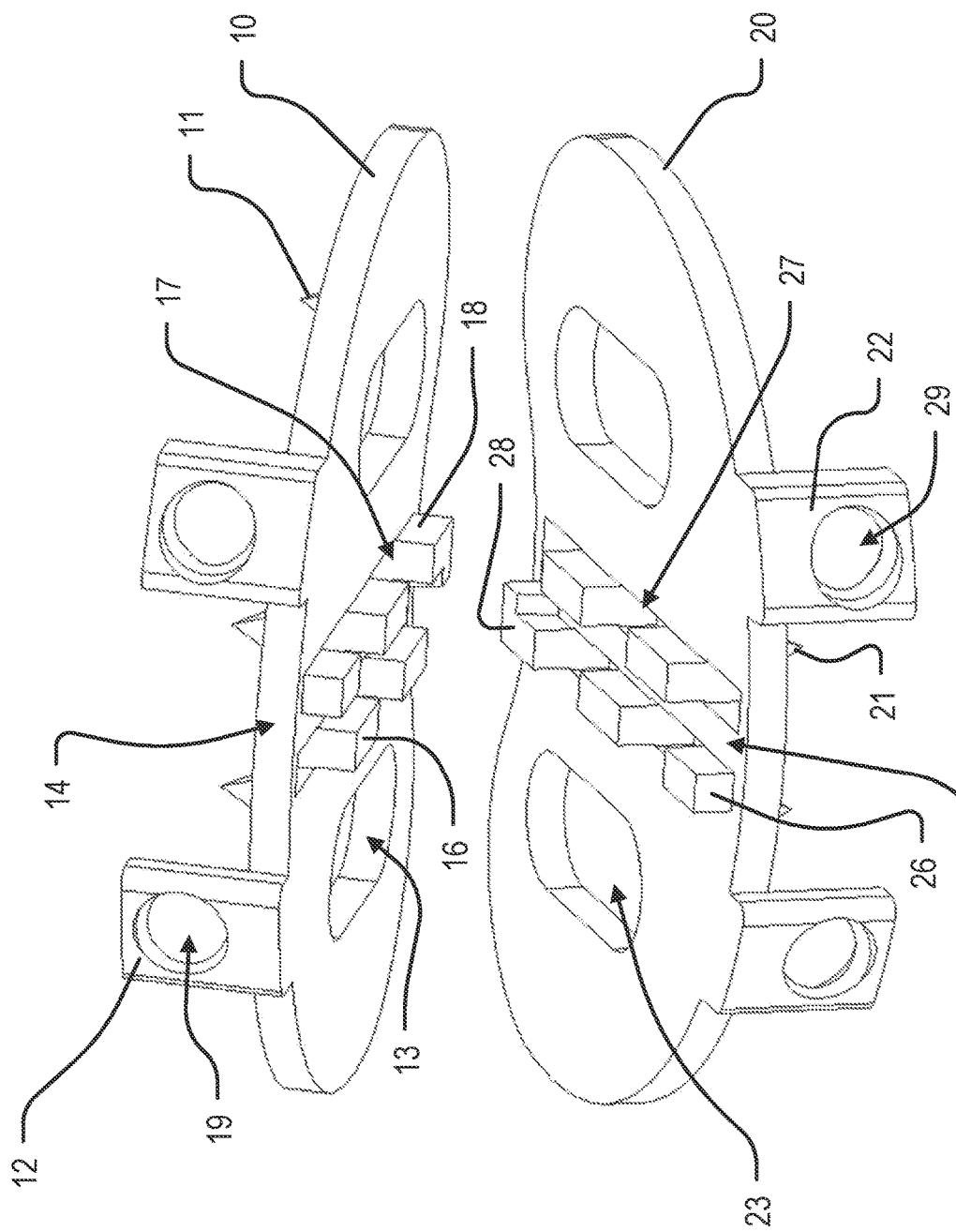
FIG. 2 is a perspective view of an expandable implant in an expanded position.
Figure 3:
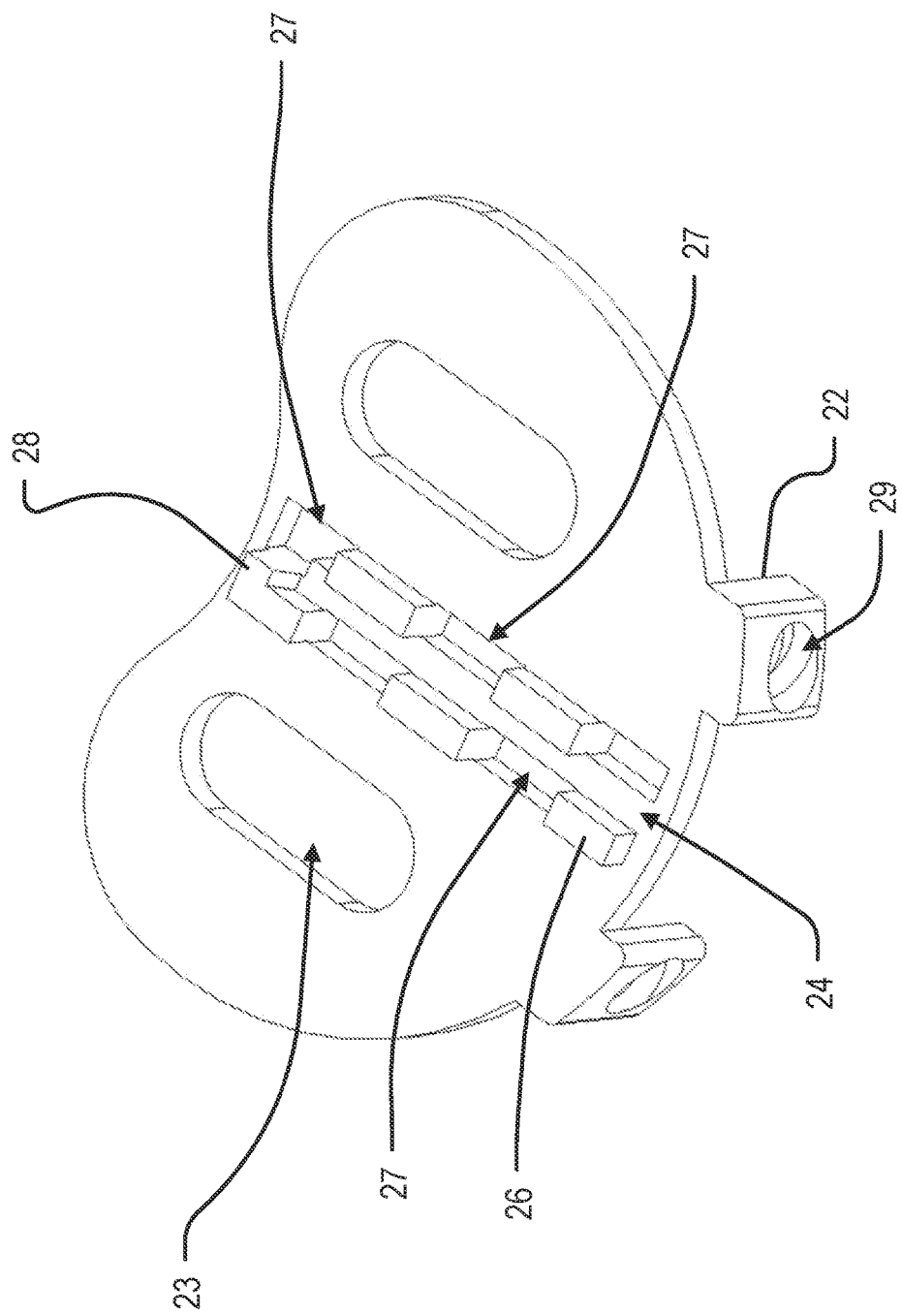
FIG. 3 is a perspective view of an inferior endplate.
Figure 4:
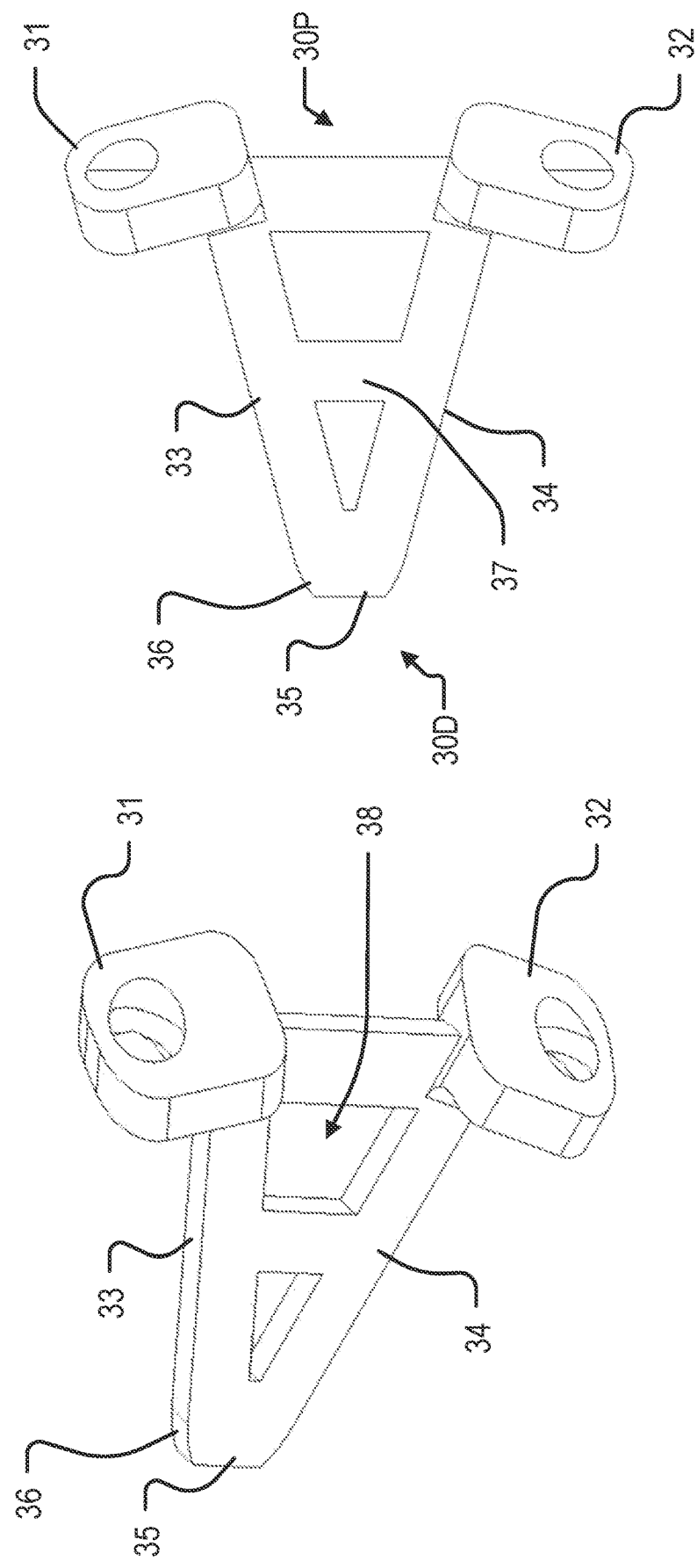
FIG. 4A is a perspective view of a shim for use with various implant embodiments.
FIG. 4B is a side view of a shim for use with various implant embodiments.

FIG. 1 is a perspective view of an expandable implant 100 in a collapsed position; FIG. 2 is a perspective view of the expandable implant 100 in an expanded position; and FIG. 3 is a perspective view of an inferior endplate 20. Various embodiments disclosed herein may be used in an Anterior Cervical Discectomy and Fusion (ACDF), an Anterior lumbar interbody fusion (ALIF), a Transforaminal lumbar interbody fusion (TLIF), or a lateral Lumbar Interbody Fusion (LLIF) procedure, for example. Additionally, some embodiments may be used to separate and/or couple other boney structures than those of the spine. In the example embodiments, implant 100 may include a superior endplate 10 and an inferior endplate 20, for example. The superior endplate 10 may include at least one eyelet 12 that defines a bone screw aperture 19. Similarly, the inferior endplate 20 may include at least one eyelet 22 that defines a bone screw aperture 29. In the example embodiment, each of the superior and inferior endplates 10, 20 include a pair of eyelets 12, 22, for example. Additionally, the eyelets 12, 22 may be disposed at a proximal end 100P of implant 100, for example. In this embodiment, implant 100 may extend in a proximal-to-distal direction from proximal end 100P to distal end 100D, for example. Additionally, implant 100 may extend in a widthwise direction between a first lateral end 100L and a second lateral end 100L, for example.

In various embodiments, the proximal-to-distal direction may refer to an insertion direction and the widthwise direction may be oriented in a perpendicular direction with respect to the proximal-to-distal direction. In some embodiments, a distance from proximal end 100P to distal end 100D may be less than a distance from first lateral end 100L to second lateral end 100L. However, other embodiments may have alternate configurations in which a distance between lateral ends 100L is less than a distance between the proximal end 100P and distal end 100D.

Figure 7:
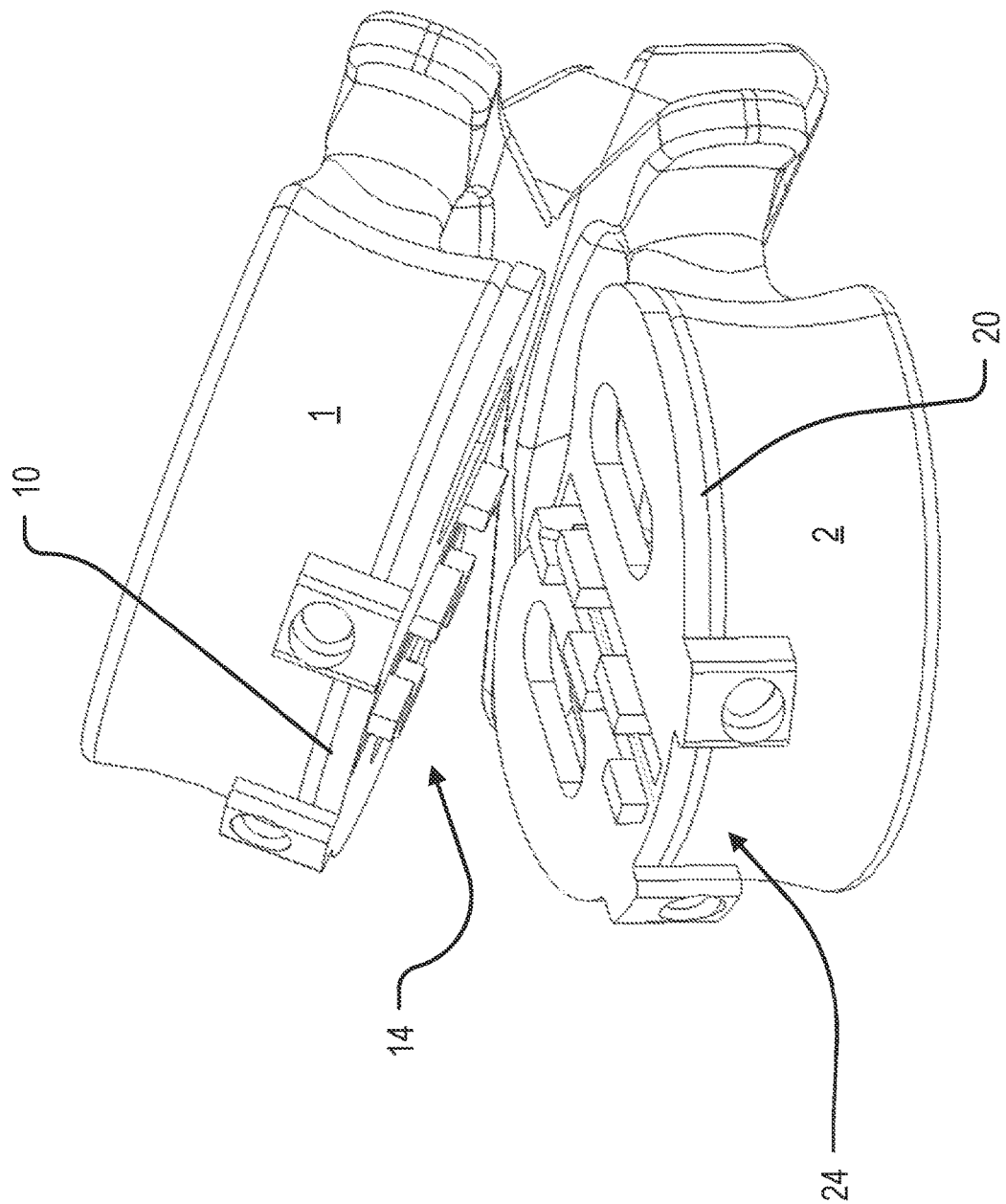
FIG. 7 is a perspective view of an expandable implant in an expanded position within a disc space.

In various embodiments, the proximal end 100P may be curved and/or have a perimeter defined by an arc of a circle substantially approximating the curvature of a disc space, e.g., see FIG. 7. Similarly, the eyelets 12, 22 may have a curved shape and/or interior surface for contacting a superior vertebrae 1 and an inferior vertebrae 2, respectively. However, in some embodiments eyelets 12, 22 may not be positioned on implant 100 to be directly in contact with a boney anatomy.

In various embodiments, the exterior surface of the superior endplate 10 and inferior endplate 20 may include various engagement features 11, 21. In the example embodiment, engagement features 11, 21 are pyramid shaped spikes, although other types of engagement features may be used in addition to or in alternative to engagement features 11, 21. For example, hooks, claws, teeth, dimples, surface texturing, cross hatching, rails, and variously shaped tread patterns to name a few. Additionally, in the example embodiment the superior endplate 10 may include at least one graft window 13 and the inferior endplate may include at least one graft window 23. In various embodiments, graft windows 13, 23 may correspond in size, shape, and position to one another such that a fusion process may be facilitated. In some embodiments, graft windows 13, 23 may have texturing and or engagement features to facilitate coupling to or holding a graft or bone growth promoting material in place.

Figure 5:
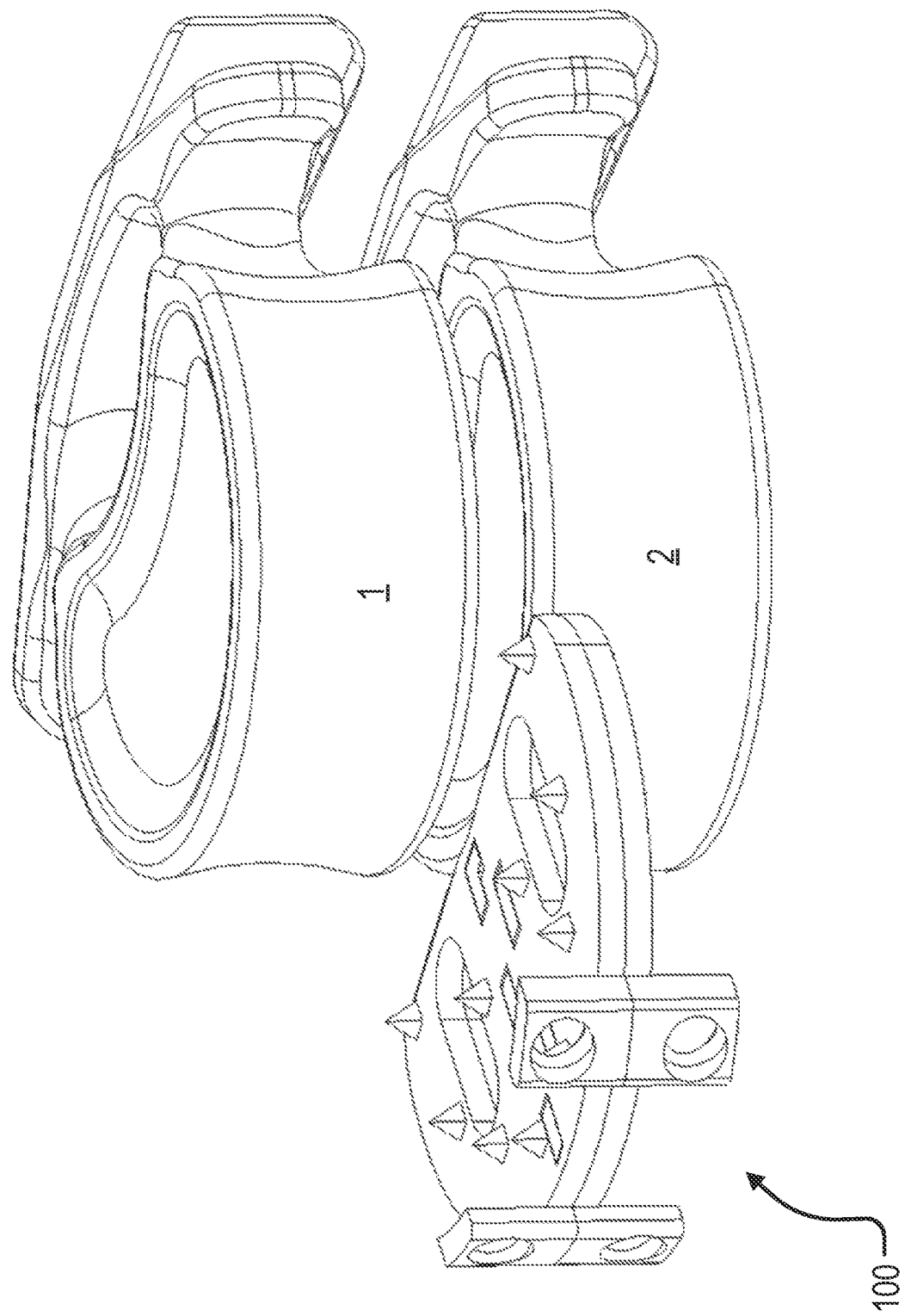
FIG. 5 is a perspective view of an expandable implant in a collapsed position for insertion within a disc space.

As seen best in FIGS. 2-3, the interior of the superior endplate 10 and inferior endplate 20 may include at least one track 14, 24, respectively. In various embodiments, the structure of tracks 14, 24 may be designed such they nest and/or mate with one another in a collapsed position. For example, as shown in FIGS. 1 and 5 the interior surfaces of superior endplate and inferior endplate 10, 20 directly contact one another in a collapsed position, e.g., they are flush with one another. This configuration may have the advantage of an implant 100 having a relatively small thickness which may aid in the insertion of implant 100 into a disc space, for example. However, other embodiments may not necessarily nest and/or mate together as shown in the FIGS. 1 and 5, for example the superior endplate 10 and inferior endplate 20 may be considered in a collapsed position even though the respective interior surfaces of endplates 10, 20 do not come into direct contact with one another and/or are not perfectly flush with one another. An example structure of tracks 14, 24 explaining how these two tracks mate together is explained below.

In this embodiment, tracks 14, 24 extend in a proximal to distal direction at a location corresponding to centerline of implant 100. However, as shown in the other embodiments, tracks 14, 24 may disposed in alternate locations and vary in number from this particular embodiment. Each track, 14, 24 may comprise a pair of rails defining a passageway or channel therebetween, for example. In the example embodiment, track 14 may comprise a series of raised block structures 16, 18 that are spaced apart by a series of corresponding apertures 17 that extend through the superior endplate 10, for example. In the example embodiment, the raised block structures 16, 18 increase in height in a proximal-to-distal direction. Additionally, the distal most block structure 18 may have an L shape defining a distal most stop feature of track 24. For example, distal most block structure 18 may stop a shim 30 in place and/or prevent shim 30 from being inserted too far through the track 14. In this way, distal most block structure 18 may include a stop wall facing the proximal end 100P and a sidewall facing a lateral end 100L. It shall be understood that in other embodiments, the heights of the raised block structures 16, 18 may be the same and/or substantially the same.

Similarly, the inferior endplate 20 may include a track 24 that extends in the proximal-to-distal direction at approximately the centerline of the implant 100. Track 24 may comprise a series of raised block structures 26, 28 spaced apart by a series of corresponding apertures 27. In the example embodiment, the raised block structures 26, 28 increase in height in a proximal to distal direction. Additionally, the distal most block structure 28 may have an L shape defining a distal most stop feature of track 24. For example, distal most block structure 28 may stop a shim 30 in place and/or prevent shim 30 from being inserted too far through the track 24. In this way, distal most block structure 28 may include a stop wall facing the proximal end 100P and a sidewall facing a lateral end 100L. It shall be understood that in other embodiments, the heights of the raised block structures 26, 28 may be the same and/or substantially the same. Those with skill in the art will appreciate that other structural shapes, e.g., structures shaped differently than block structures 16, 18 and 26, 28 may be used while still maintaining the inventive aspects of this disclosure. For example, pins, rods, through holes, dovetail grooves, squares, ovals, cross-shaped structures, and etc.

In the example embodiment, track 14 and track 24 may be similarly designed and coordinate together as if mirror images of one another. For example, track 14 and track 24 may be identical in form to another, but with the respective structures in a reversed orientation. Some example advantages of this configuration may be ease of assembly in an operating theater, manufacturing ease, and shipping logistics. However, in other embodiments the shape and orientation of the raised block structures and corresponding apertures of the superior endplate 10 are not necessarily the same (or mirrored images) of the inferior endplate 20. In various embodiments, the apertures 27 of the inferior endplate 20 may substantially correspond in size and shape to the size and shape of the raised block structures 16, 18 of the superior endplate 10. Similarly, the apertures 17 of the superior endplate 10 may substantially correspond in size and shape to the size and shape of the raised block structures 26, 28 of the inferior endplate 20, for example. As used in this context, the term substantially shall mean nearly or approximately while not necessarily requiring an exact friction fit. Some example types of friction fit between raised block structures 16, 18, 26, 28 may be detents, pawls, grooves, and/or grooves and channeling. However, an exact fit where the apertures 17, 27 frictionally engage and contact with corresponding raised block structures 26, 28 is also encompassed by this meaning. Additionally, it shall be understood that a depth of apertures 17, 27 as measured through endplates 10, 20 need not correspond 1:1 to a height of block structures 16, 18, 26, and 28 but that in various embodiments a depth of apertures 17, 27 may be substantially equal to a height of block structures 16, 18, 26, and 28, for example. Furthermore, in various embodiments detents and other one-way retaining features may be used between the insides of tracks 14, 24 to facilitate securing shims 30 within an interior space defined by the superior endplate 10 and inferior endplate 20.

Figure 9A:
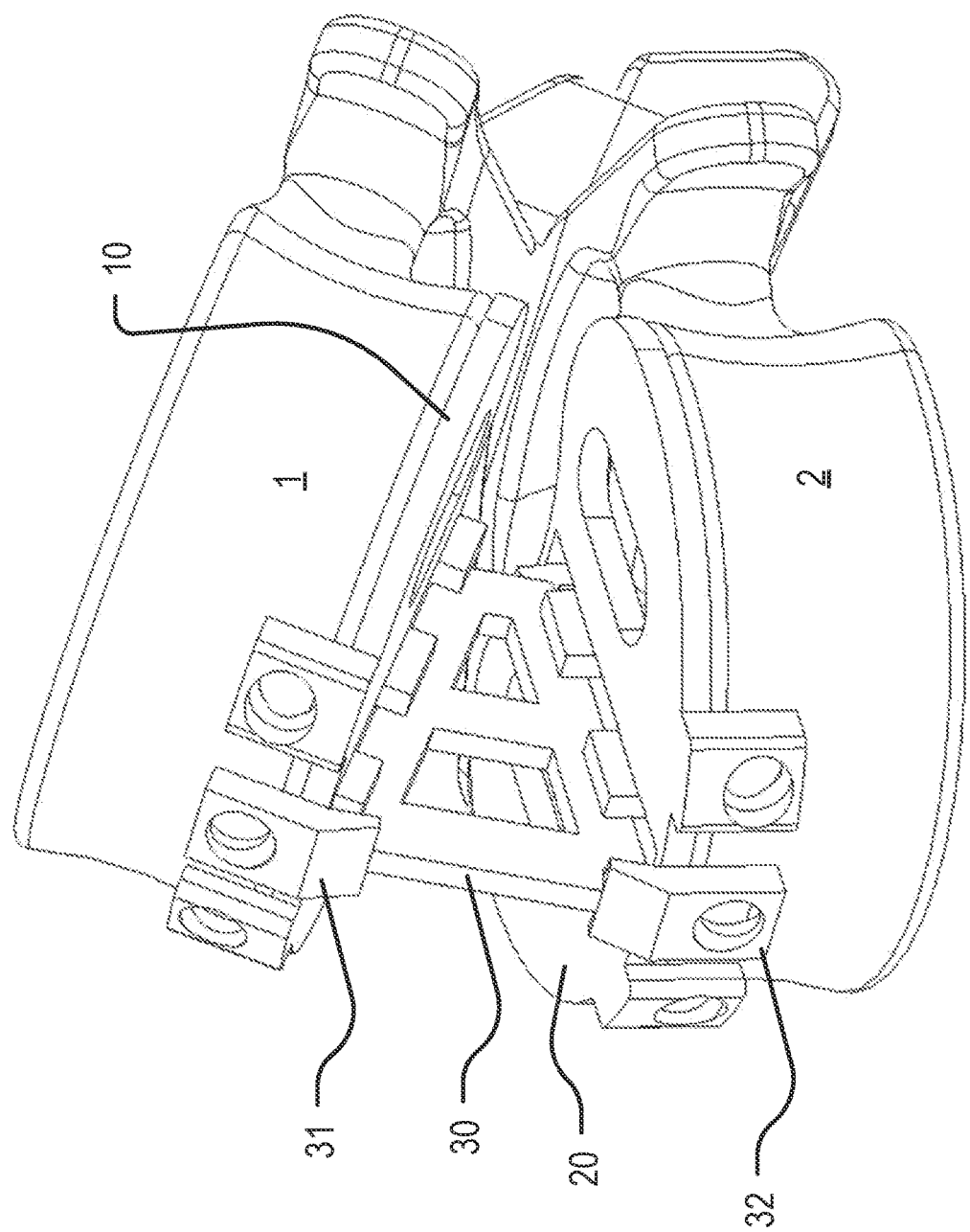
FIG. 9A is a perspective view of a shim positioned in a track of an expandable implant.

FIG. 4A is a perspective view of a shim 30 and FIG. 4B is a side view of a shim 30 for use with various implant embodiments. The example shim 30 may extend from a proximal end 30P to a distal end 30D and may include a superior eyelet 31 and an inferior eyelet 32 at the proximal end 30P, and a nose portion 35 at a distal end 30D, for example. In the example embodiment, each eyelet 31, 32 comprises a bone screw aperture for securing a bone screw therein. Additionally, the nose portion 35 may include chamfered edges 36 that may facilitate insertion of shim 30 within tracks 14, 24. In some embodiments, chamfered edges 36 may be more emphasized or drastic than the particular chamfered edges 36 shown in the corresponding FIGS. Additionally, in some embodiments chamfered edges 36 may be referred to as "lead-ins" by those with skill in the art. In various embodiments, when shim 30 is fully inserted within a disc space, eyelets 31, 32 may contact an adjacent vertebrae, for example as shown in FIG. 9A. In this embodiment, shim 30 may have a greater relative height at the proximal end 30P than at the distal end 30D. In this way, shim 30 may define the angle of inclination of the superior endplate 10 and inferior endplate 20 and a distance between the endplates 10, 20 at the proximal end 100P and distal end 100D of implant. Furthermore, the specific shim 30 used for a particular surgery may be chosen in advance based on pre-operative planning and assessment of the patient and the shim 30 may be used to adjust a kyphotic angle and/or a lordotic angle of implant 100 (depending on angle of insertion of implant 100 into the disc space).

Shim 30 may also include a superior bearing surface 33 and an inferior bearing surface 34, for example. In various embodiments, in an expanded configuration of implant 100 superior bearing surface 33 may be disposed within track 14 of superior endplate 10 and inferior bearing surface 34 may be disposed within track 23 of inferior endplate 20. In this way, superior bearing surface 33 supports the superior endplate 10 and the inferior bearing surface 34 supports the inferior endplate 20 such that implant 100 will not collapse and can properly support the adjacent vertebrae. Shim 30 may further include a stabilizing strut 37 (may also be referred to as a "joist," "brace," or "column") for added structural stability. In this embodiment, a pair of apertures 38 are disposed on opposite sides of strut 37. At least one advantage of apertures 38 is that they may facilitate a fusion process and/or allow injectable graft material to flow therethrough. In some embodiments, the strut 30 may be a solid monolithic component without apertures 38. In this alternative embodiment, the sidewalls may function like a curtain wall and contain graft material within the implant. In this illustrated embodiment, the superior and inferior bearing surfaces extend the entire length of the respective endplate 10, 20. At least one advantage of this configuration may be a relatively uniform and even distribution of loading across those surfaces which may eliminate, reduce, and/or suppress "point loading." However, in other embodiments, bearing surfaces 33, 34 may be discontinuous and/or the corresponding tracks may be discontinuous. In this alternate embodiment, the discontinuity may from a type of fulcrum point, or pivot point, that may facilitate angulation of the endplates 10, 20 with respect to one another, for example.

Figure 6:
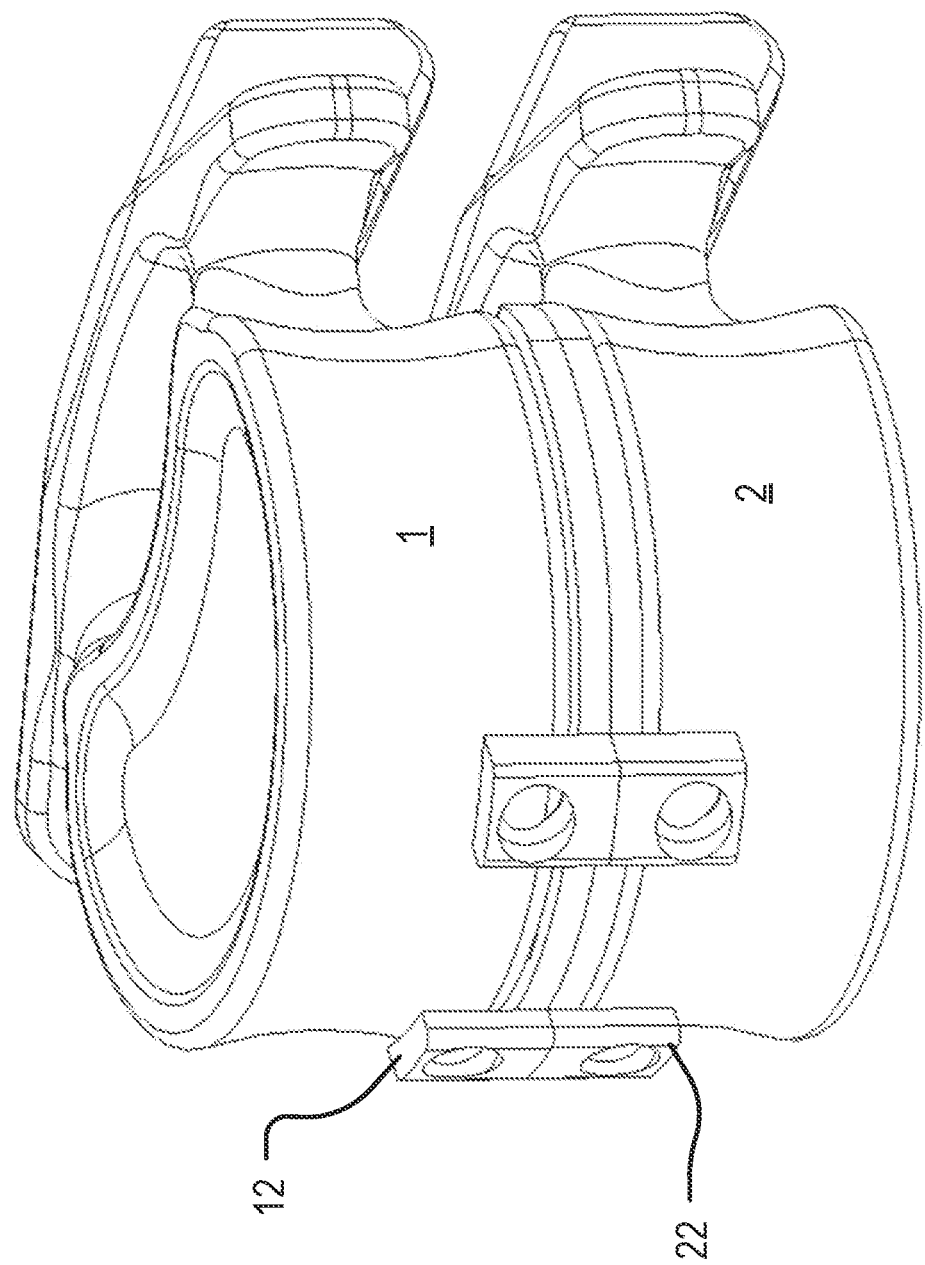
FIG. 6 is a perspective view of an expandable implant in a collapsed position after being inserted within a disc space.
Figure 8:
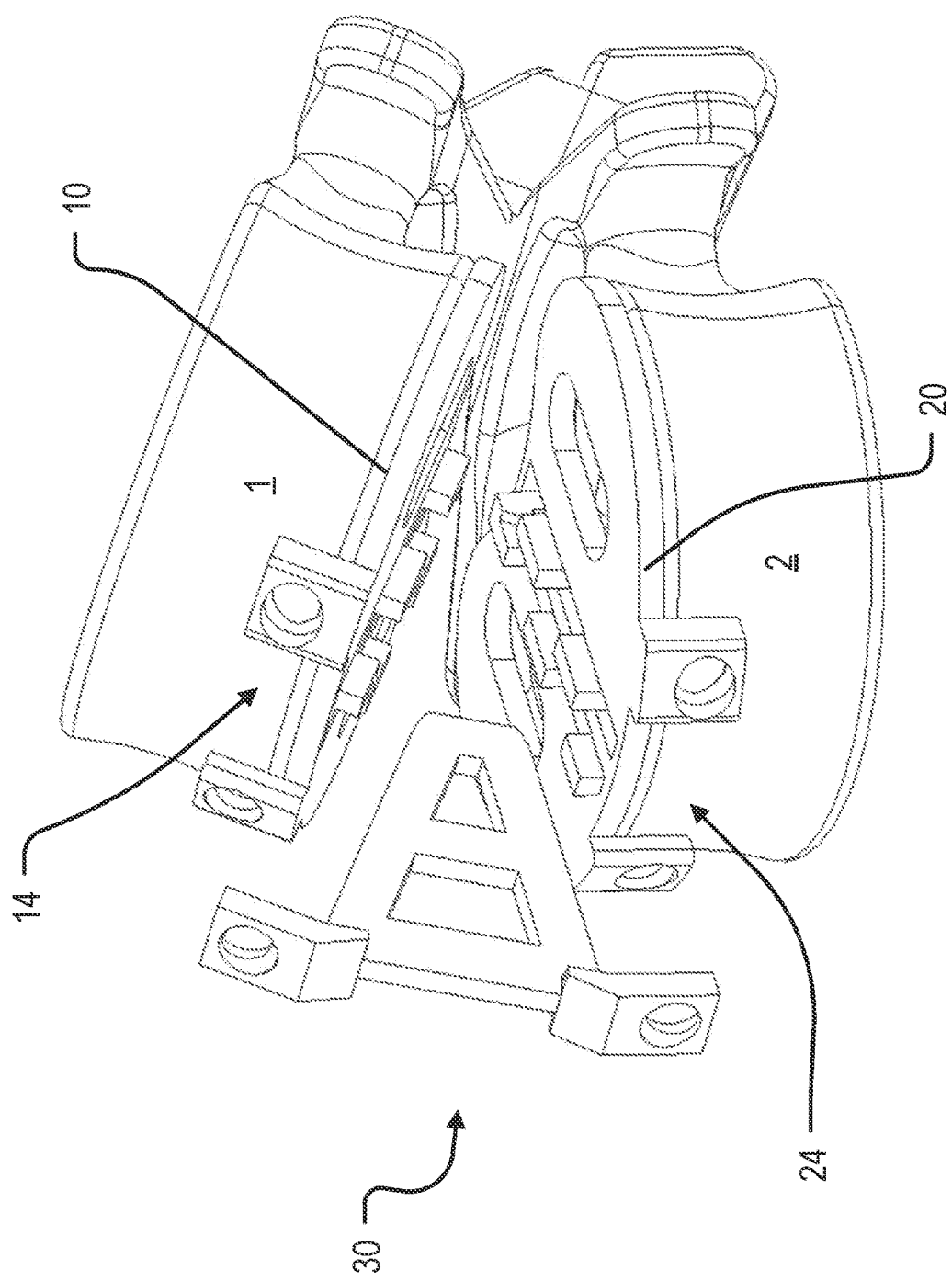
FIG. 8 is a perspective view of a shim being inserted into a track of an expandable implant.

FIG. 5 is a perspective view of an expandable implant 100 in a collapsed position for insertion within a disc space and FIG. 6 is a perspective view of the expandable implant 100 after being inserted within a disc space. As shown in FIG. 6, in some embodiments eyelets 12, 22 may rest against and/or nearly contact an adjacent vertebrae, for example superior vertebrae 1 and/or inferior vertebra 2. FIG. 7 is a perspective view of an expandable implant 100 in an expanded position within a disc space, and FIG. 8 is a perspective view of a shim 30 being inserted into the tracks 14, 24 of expandable implant 100. In operation, an end user such as a surgeon may expand implant 100 with a surgical tool such as a distractor or by an implant inserter such as the implant inserter disclosed in U.S. application Ser. No. 17/307,578, the entire contents of which are incorporated herein by reference. Likewise, the endplates 10, 20 may be insert into the disc space by a surgical tool, such as forceps or by an implant inserter such as the implant inserter disclosed in U.S. application Ser. No. 17/307,578. In at least one embodiment, an implant inserter may expand a spacing between the superior endplate 10 and inferior endplate 20 and a carriage, movable in a proximal to distal direction, may linearly translate forward for inserting shim 30 within implant 100, for example. Additionally, in various embodiments implant 100 may comprise detents, sockets, grooves, etc. for grasping of implant 100 by a corresponding inserter, for example.

After the endplates 10, 20 are positioned within the disc space, shim 30 may be insert into the interior of implant 100 in an aligned position with tracks 14, 24, for example. The surgeon may push shim 30 in a proximal to distal direction until nose 35 contacts the stop surfaces of structural blocks 18, 28. In doing so, shim 30 may also further distract and/or initially distract the disc space, i.e., expand the disc space. As explained above, the superior endplate 10 may be supported by the superior bearing surface 33 and the inferior endplate 20 may be supported by the inferior bearing surface 34. Additionally, an angle of repose of shim 30 may be defined by a line extending parallel with the superior bearing surface 33 and a line extending parallel with the inferior bearing surface 34. For example, an interior angle at a region where the two lines intersect. Therefore, shim 30 may, in turn, define a kyphotic angle and/or lordotic angle of implant 100.

Figure 9B:
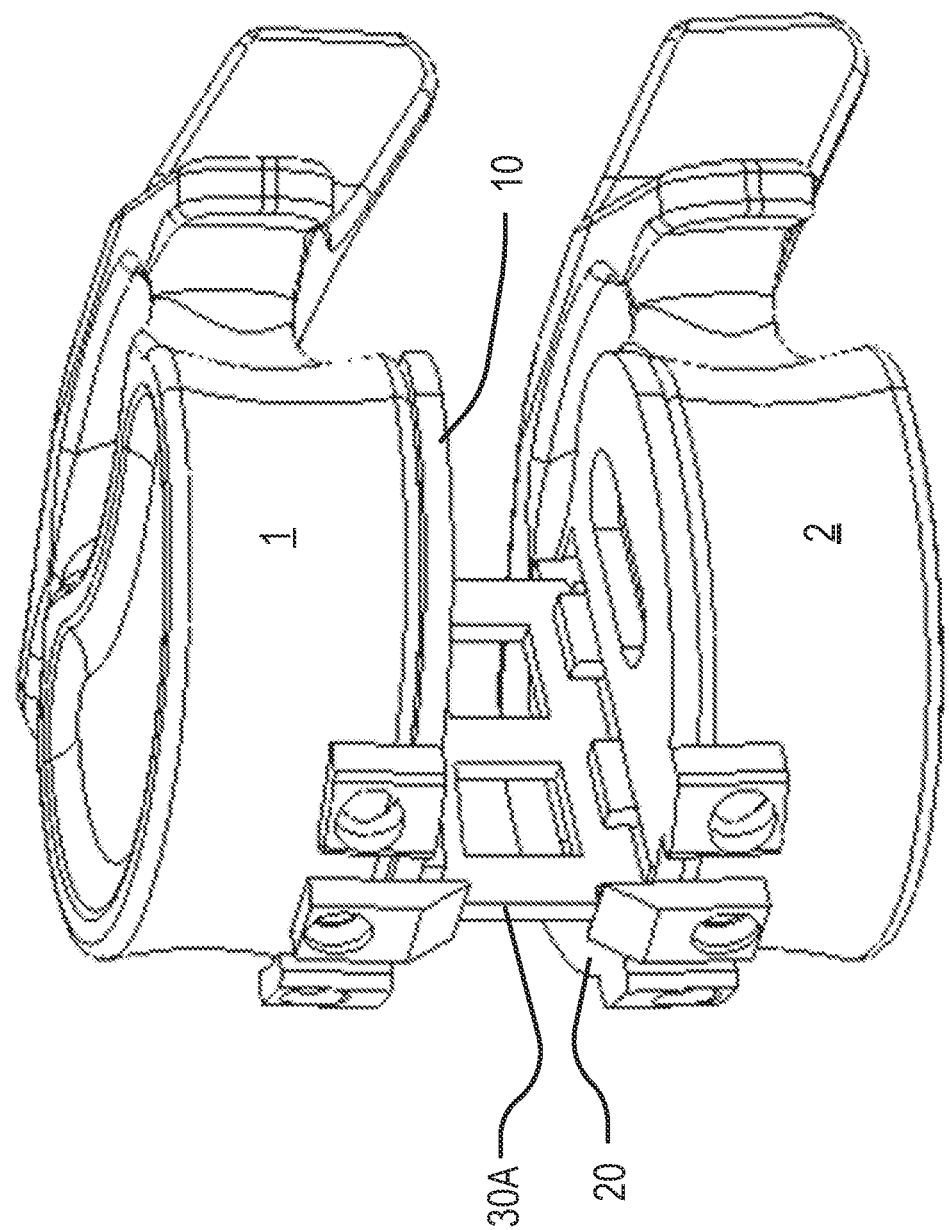
FIG. 9B is a perspective view of an alternate shim positioned into a track of an expandable implant.

FIG. 9A is a perspective view of shim 30 positioned in a fully installed position within tracks 14, 24. FIG. 9B is a perspective view of an alternate shim 30A positioned into a track of an expandable implant. Alternate shim 30A may have the same, similar, and/or substantially the same features and functionality as explained above with respect to shim 30. In this embodiment, shim 30A may have a relatively greater height at a distal end 30D when compared to shim 30. For example, shim 30A may provide less of an angle of repose such that the kyphotic and/or lordotic angle is less than when shim 30 is used.

Figure 10:
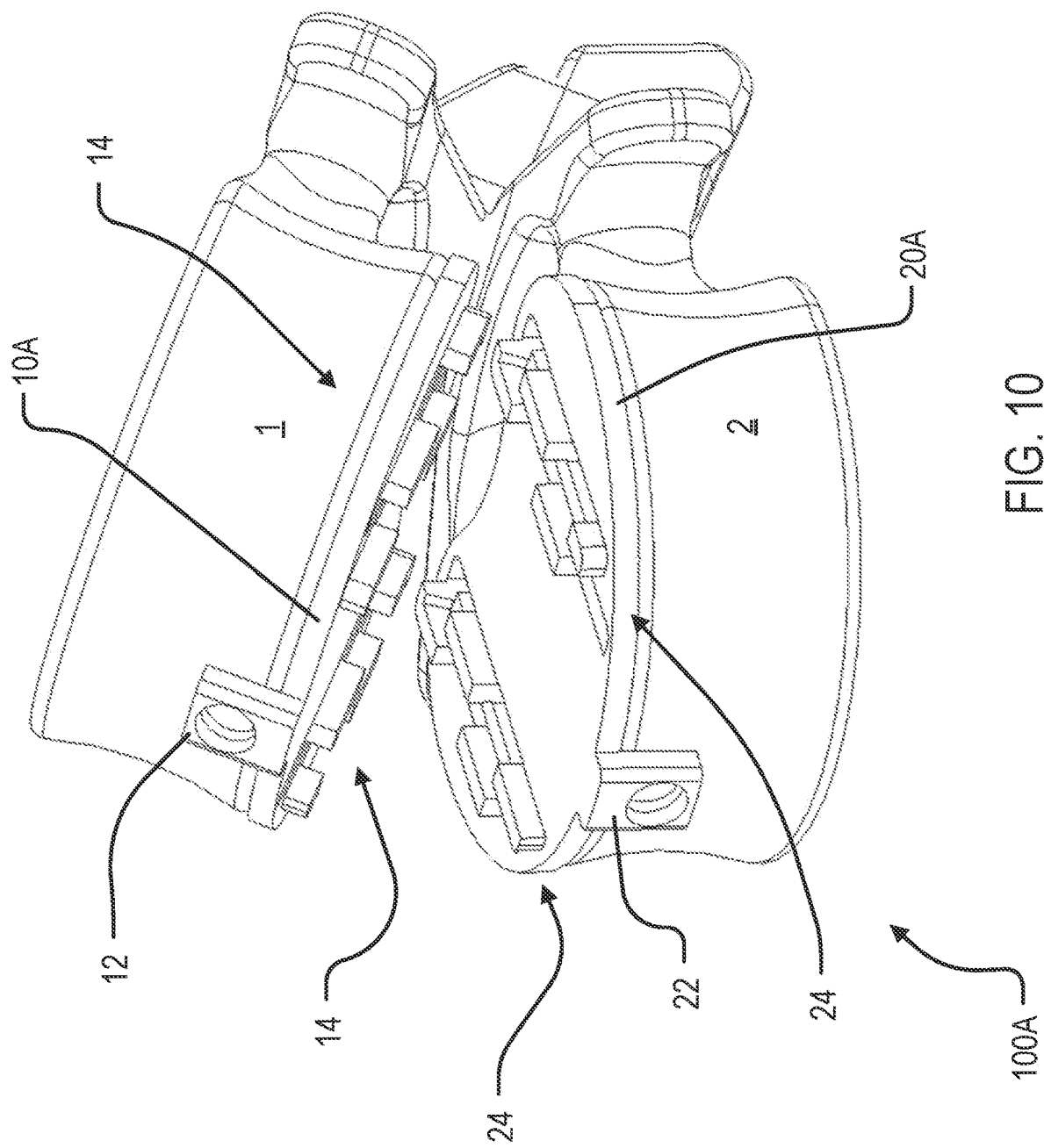
FIG. 10 is a perspective view of an alternate embodiment of an expandable implant.
Figure 11:
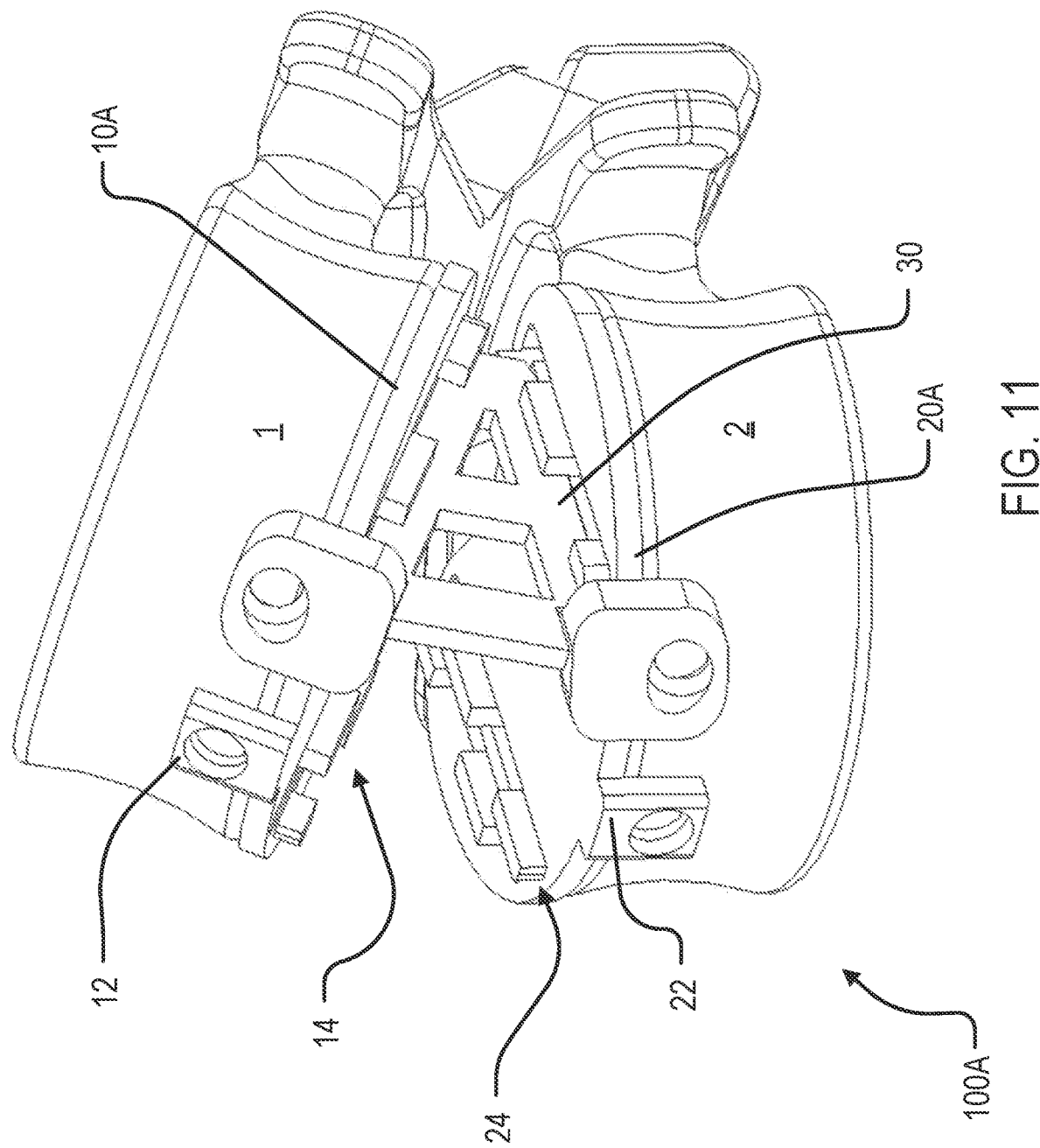
FIG. 11 is a perspective view of a first shim being inserted in the expandable implant embodiment of FIG. 10.
Figure 12A:
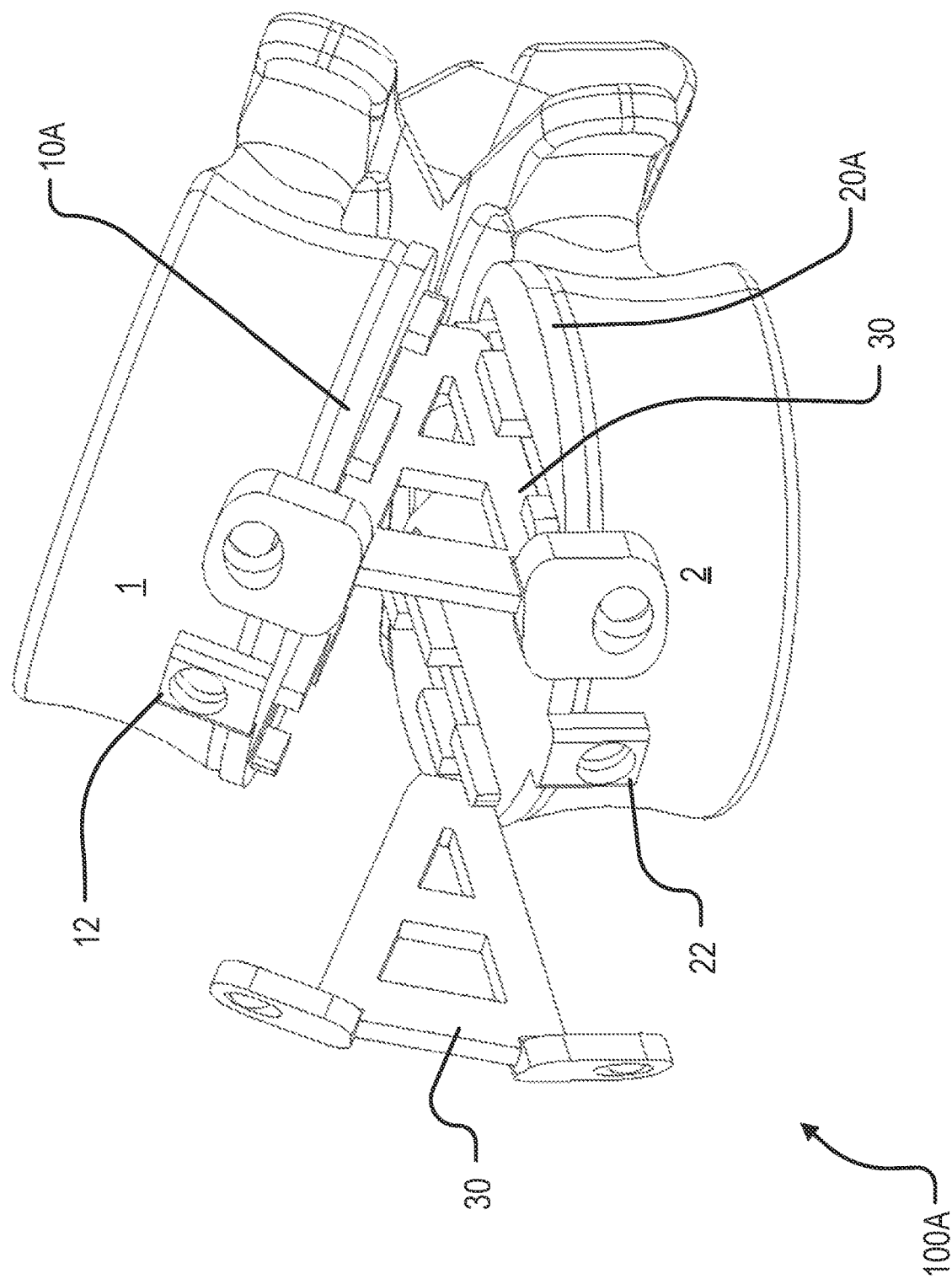
FIG. 12A is a perspective view of a second shim being inserted in the expandable implant embodiment of FIG. 10.

FIG. 10 is a perspective view of an alternate embodiment of an expandable implant 100A including a superior endplate 10A having at least two superior tracks 14 and an inferior endplate 20A having at least two inferior tracks 24. Implant 100A may have the same, similar, and/or substantially the same features and functionality as explained above with respect to implant 100. In this embodiment, the superior endplate 10A includes a single eyelet 12 disposed in a central portion of the proximal end 100P and the inferior endplate 20A includes a single eyelet 22 in a central portion of the proximal end 100P, e.g., eyelets 12, 22 may be aligned with a midsection and/or centerline of implant 100A. Additionally, the superior endplate 10A and inferior endplate 20A may each include a pair of tracks 14, 24 disposed on opposite sides of the centerline of implant 100. FIG. 11 is a perspective view of a first shim 30 being inserted in the expandable implant 100A embodiment of FIG. 10. FIG. 12A is a perspective view of a second shim 30 being inserted in the expandable implant embodiment of FIG. 10.

Figure 12B:
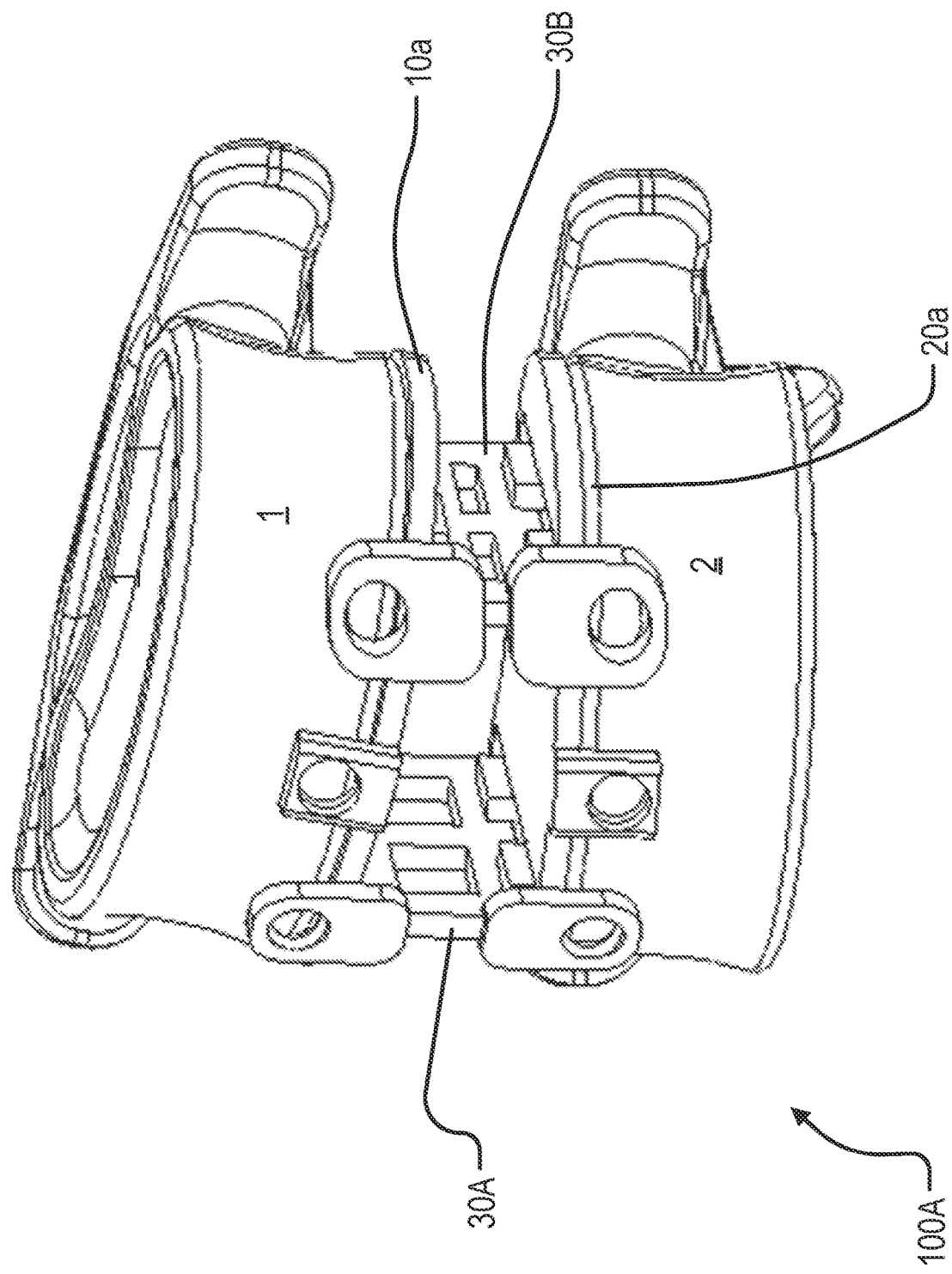
FIG. 12B is a perspective view of an alternate first shim and an alternate second shim in an installed position in the expandable implant embodiment of FIG. 10.

FIG. 12B is a perspective view of an expandable implant 100A that may distract a disc space and adjust an angle of inclination between a superior vertebrae 1 and an inferior vertebrae 2. For example, implant 100A may adjust the disc space in both the sagittal plane and in the coronal plane, see FIG. 25. For example, implant 100A may utilize a first shim 30A having a relatively large height and a second shim 30B having a relatively smaller height. For example, shim 30A may comprise a first height at a proximal end 100P and a second height at a distal end 100D and shim 30B may comprise a third height at a proximal end 100P and a fourth height at a distal end 100D. In this embodiment, the first height is greater than the second height, third height, and fourth height. Additionally, the second height is greater than the third height and fourth height and the third height is greater than the fourth height. Those with skill in the art will appreciate that the exact geometry of shims 30A and 30B are variable and can be adjusted to suit the particular needs of a specific patient, for example. Accordingly, shims 30A and 30B may take any size and shape, i.e., comprise virtually any angle of inclination and or height.

Figure 13:
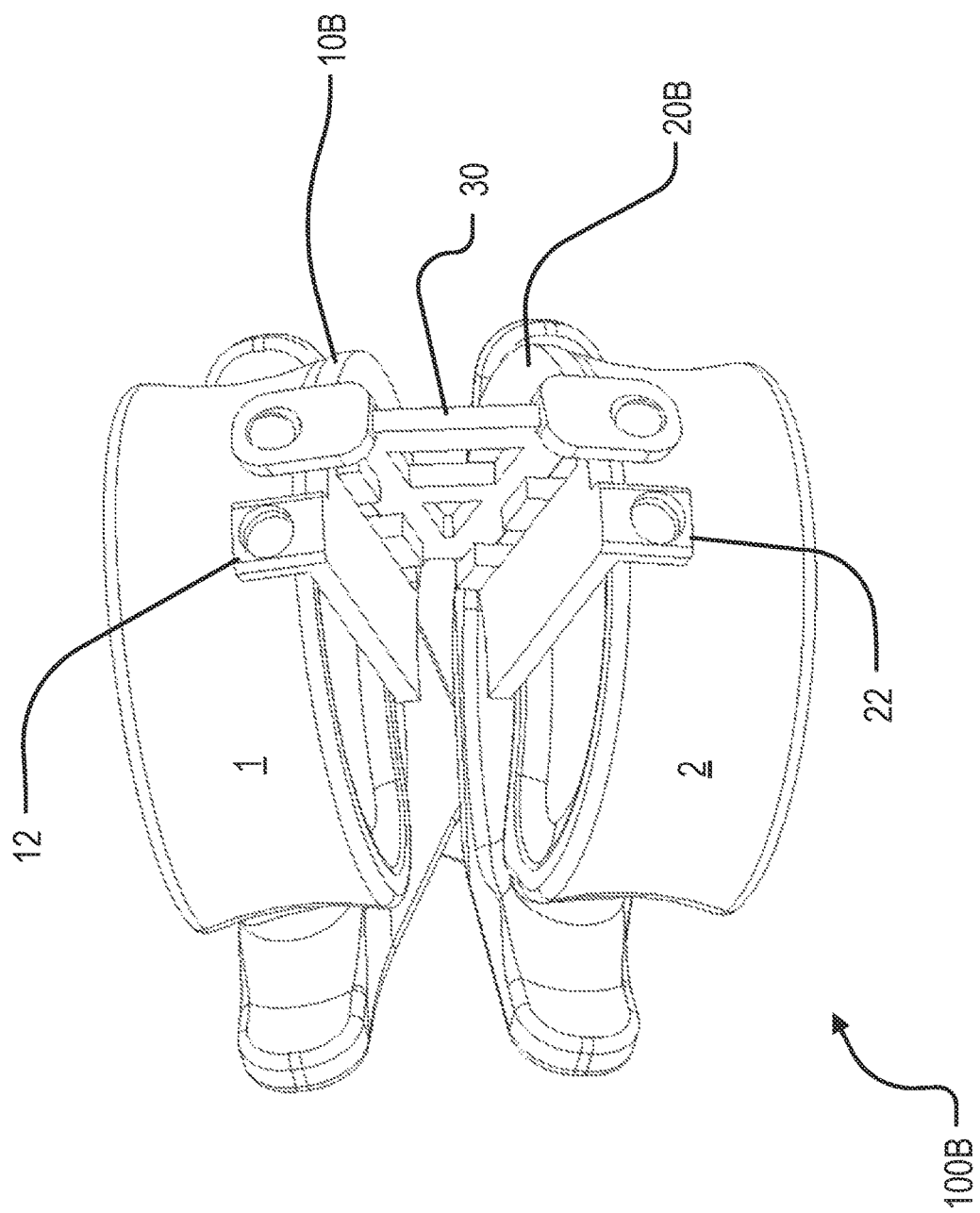
FIG. 13 is a perspective view of an alternate embodiment of an expandable implant.

FIG. 13 is a perspective view of an alternate embodiment of an expandable implant 100B. Implant 100B may be used for a hemicorpectomy surgery, for example. In various embodiments, implant 100B may be similar to implant 100A but with one side of implant 100A removed, for example a first lateral side after eyelets 12, 22. Implant 100B may retain the same and/or have a similar functionality as previously explained with reference to implants 100 and 100A, for example. In some embodiments, implant 100B may be a discrete portion of implant 100A. For example, implant 100A may include a seam or fracture joint which can be broken to yield the implant 100B as shown in FIG. 13.

Figure 14:
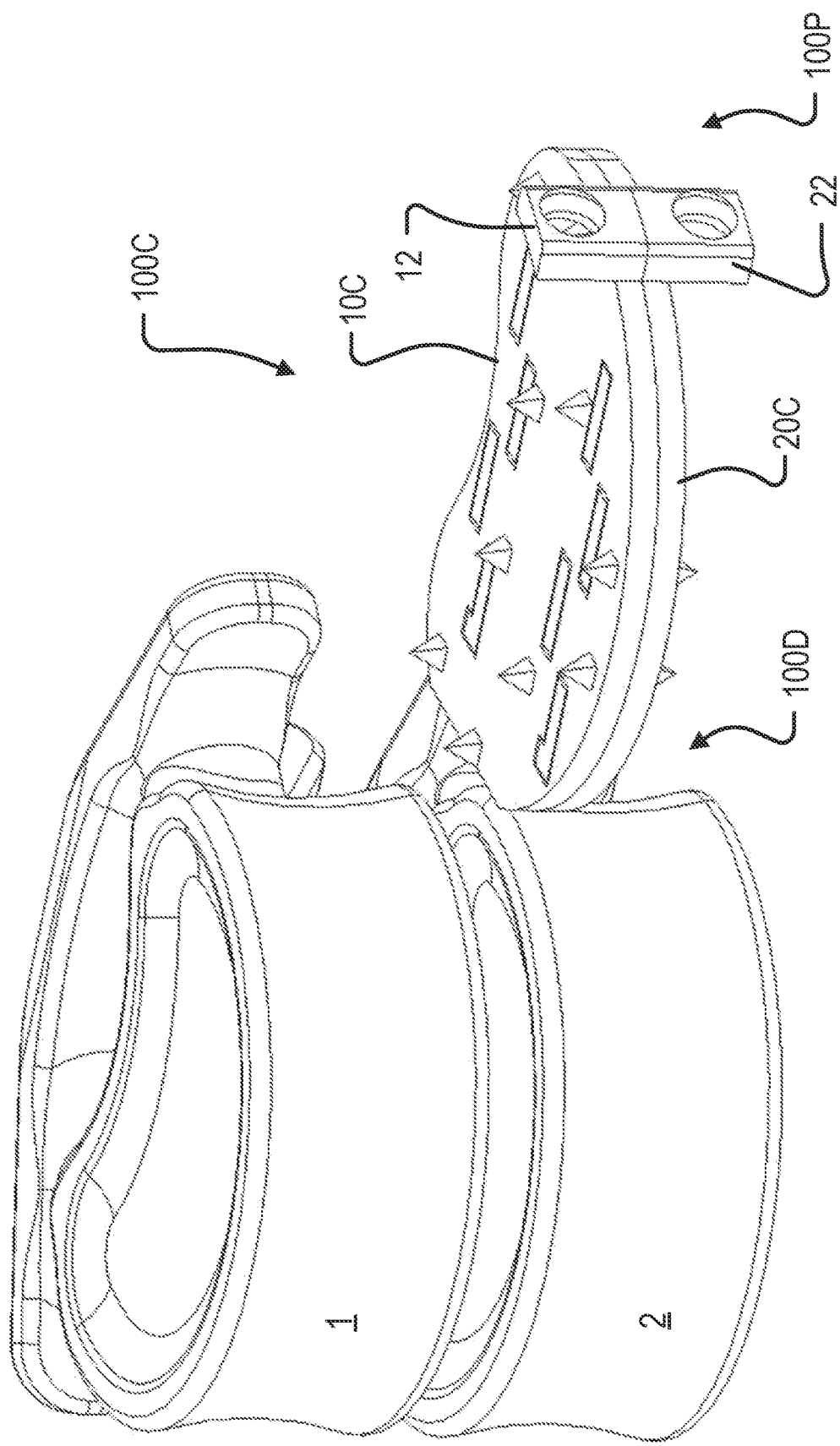
FIG. 14 is a perspective view of an alternate embodiment of an expandable implant in a collapsed position before insertion into a disc space.
Figure 15:
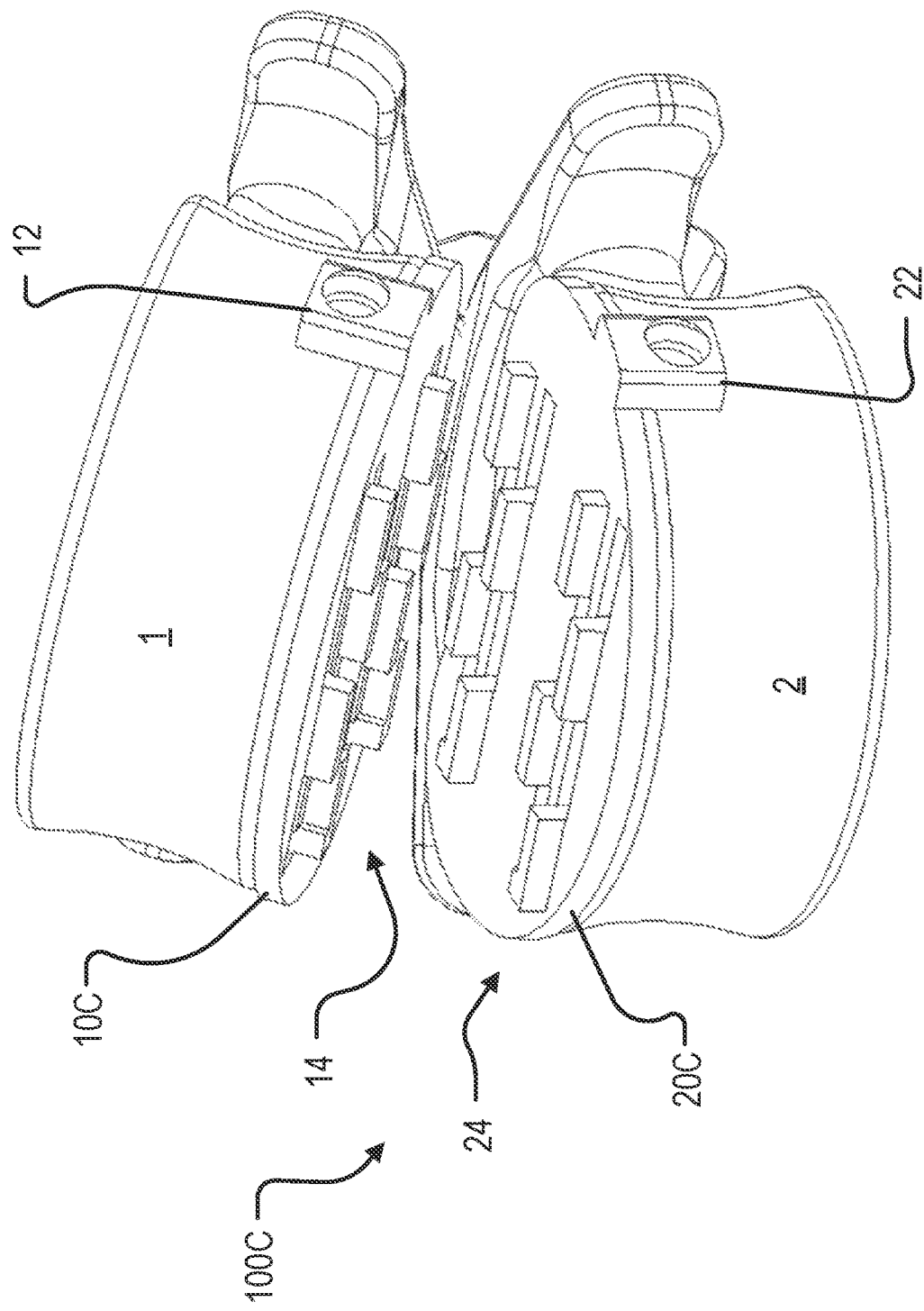
FIG. 15 is a perspective view of the embodiment of FIG. 14 in an expanded position in a disc space.
Figure 16:
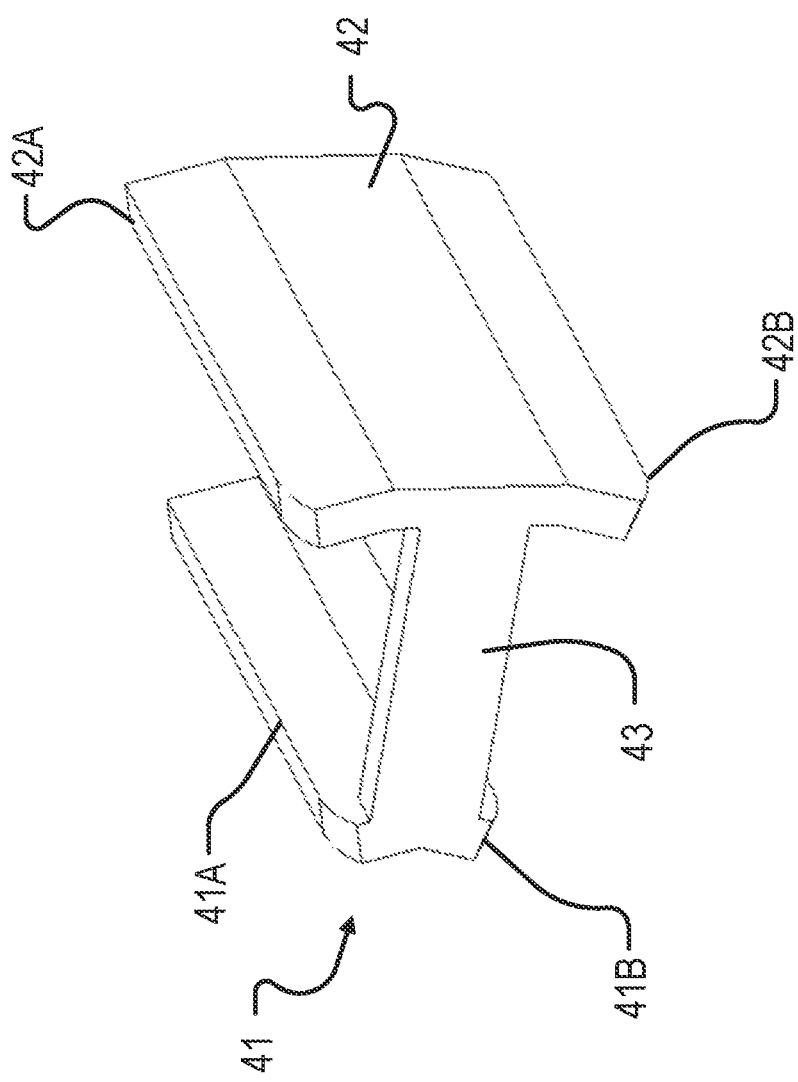
FIG. 16 is a perspective view of a shim for use with the embodiment of FIGS. 14 and 15.
Figure 17:
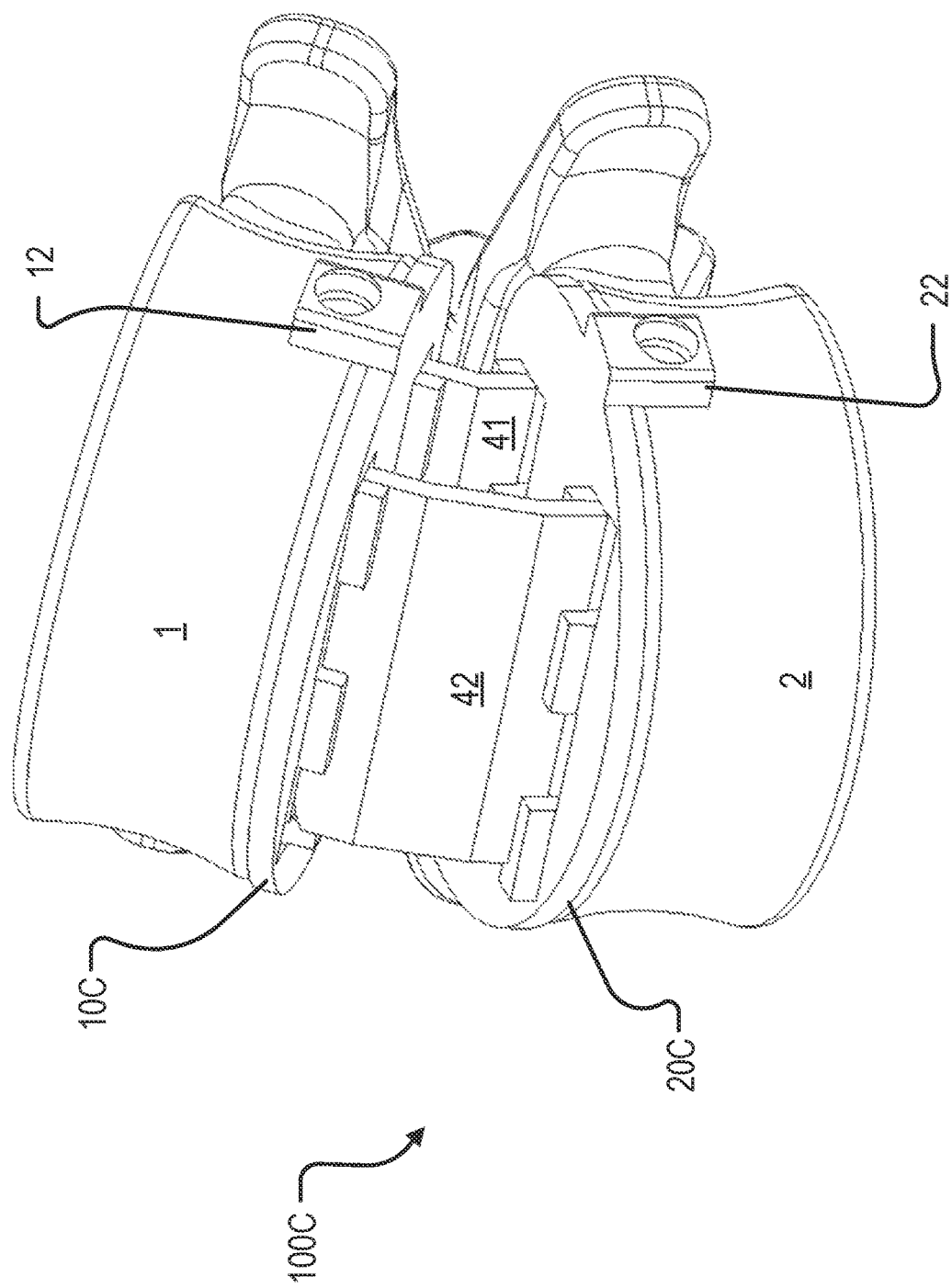
FIG. 17 is a perspective view of the shim of FIG. 16 in an installed position within an expandable implant.

FIG. 14 is a perspective view of an alternate embodiment of an expandable implant 100C in a collapsed position; FIG. 15 is a perspective view of the embodiment of FIG. 14 in an expanded position in a disc space; FIG. 16 is a perspective view of a shim 40; and FIG. 17 is a perspective view of the shim of 40 in an installed position within an expandable implant 100C. Referring generally to FIGS. 14-17, implant 100C may be configured for insertion into a disc space from a lateral perspective, for example a lateral lumbar interbody fusion surgery. In the example embodiment, implant 100C may include the same, similar, and/or substantially similar features and functionality as previously explained. In this embodiment, implant 100C may include a superior endplate 10C and an inferior endplate 20C that extend in a proximal-to-distal direction from a proximal end 100P to a distal end 100D. Additionally, superior endplate 10C and inferior endplate 20C may each include a pair of tracks 14, 24 having similar features and functionality as previously explained. Furthermore, in this embodiment, implant 100C may include a superior eyelet 12 and an inferior eyelet 22 that contact a boney anatomy as shown in FIG. 15, for example. Additionally, in various embodiments, superior eyelet 12, and inferior eyelet 22 may be recessed differently than shown in the corresponding FIGS. In some embodiments, superior eyelet 12 and 24 may extend oppositely from the orientation show in the corresponding FIGS., e.g., superior eyelet 12 may extend toward inferior endplate 20 and inferior eyelet 23 may extend toward superior endplate 10. Therefore, when implant 100 is expanded the eyelets 12, 24 may be between the superior vertebrae and inferior vertebrae, respectively. Similarly, in this alternate embodiment, eyelets 12, 24 may be offset from one another and a corresponding aperture (or apertures) may be formed in the superior endplate 10 and inferior endplate 20 such that implant 100 may fully collapse in similar fashion as shown in the various illustrations herein.

FIG. 16 illustrates a multi-track shim 40 that may be configured for insertion in each of the pair of tracks 14 and pair of tracks 24, for example. In this embodiment, shim 40 comprises a first sidewall 42 including a superior bearing surface 42A and an inferior bearing surface 42B. Similarly, shim 40 comprises a second sidewall 41 including a superior bearing surface 41A and an inferior bearing surface 41B. Shim 40 may include a reinforcing strut 43 for reinforcing a structural integrity of shim 40. Reinforcing strut 43 may be disposed at a distal end of strut 40 and be positioned between the superior bearing surfaces 41A and 41B and inferior bearing surfaces 42A, 42B such that it will not interfere with tracks 14, 24. In this embodiment, a relative height of the first sidewall 42 is greater than a relative height of the second sidewall 41. Additionally, in various embodiments a relative height of any one of the first and second sidewall 41, 42 may be greater at a proximal end when compared to a distal end and vice versa. In some embodiments, shim 40 may not include a reinforcing strut and instead may be formed of separate pieces. For example, a first section of shim 40 corresponding to the distal end, a second section of shim 40 corresponding to a medial portion, and a third section of shim 40 corresponding to the proximal end. In another similar embodiment, a first superior portion extending the full length and a second inferior portion extending the full length may be provided. At least one advantage of these configurations may be that the separable pieces facilitate a gradual correction of the segment. In this embodiment, a surgeon may insert a first portion and access the mobility of the target segment, and if needed the surgeon may place a second portion to increase a distraction and/or angulation of the segment, e.g., the second segment may increase the posterior height view of the resulting anterior height. Similarly, in some embodiments a surgeon may insert a first shim 40 to perform an initial distraction and then adjust the shim 40 to change the particular angle of inclination of the superior and inferior vertebrae and/or the relative distraction between the superior and inferior vertebrae. It shall be understood that embodiments in accordance with the disclosure herein, contemplate a method of operation and a corresponding implant 100 in which shims 40 may be insert and adjusted and/or taken out depending on the progress of the surgery and the particular needs determined by the surgeon at the time of surgery and/or even in advance of surgery during pre-operative planning.

Figure 18:
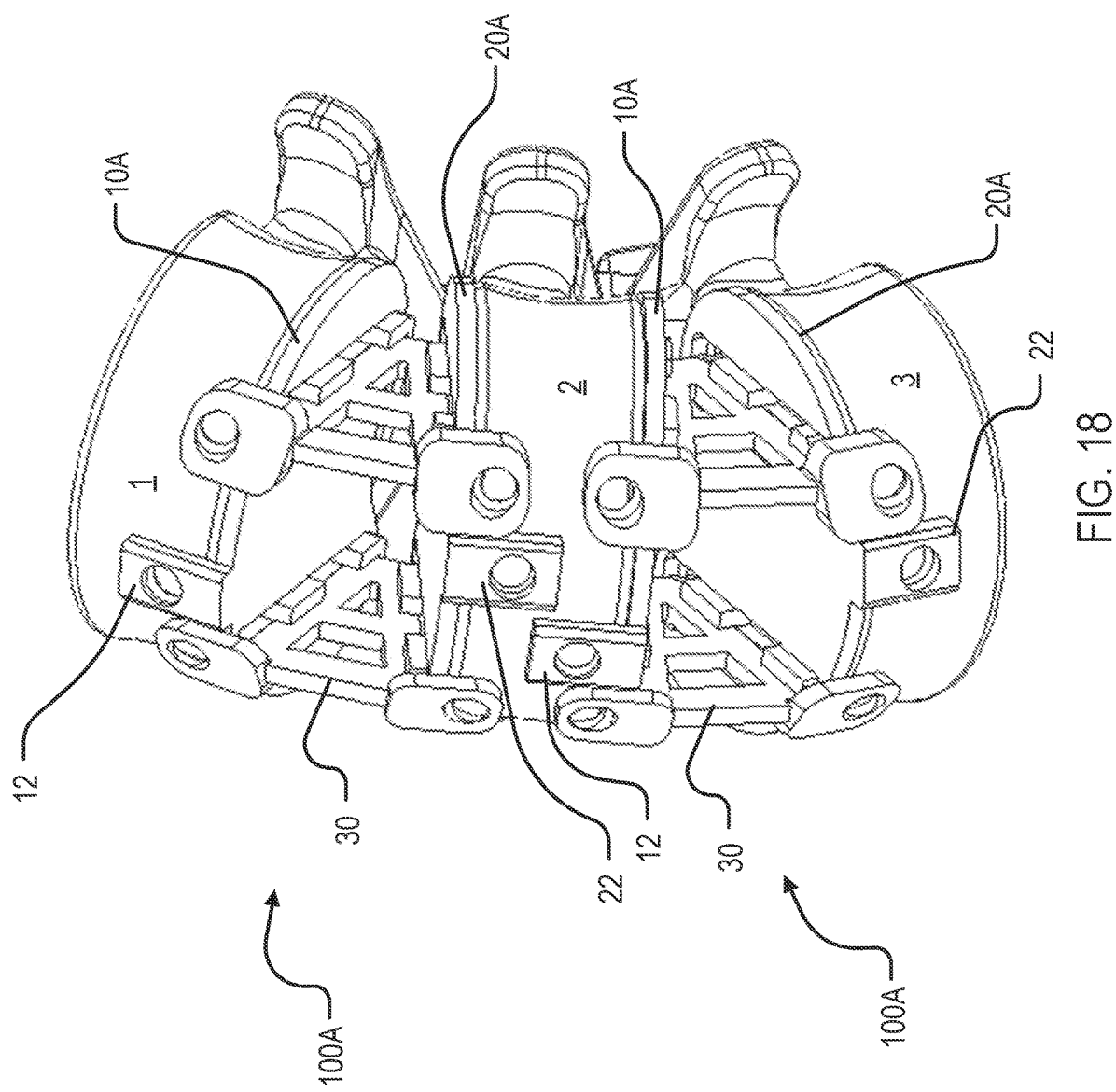
FIG. 18 is a perspective view of a first and second expandable implant being used for a multi-level surgery.

FIG. 18 is a perspective view of a first expandable implant 100A and second expandable implant 100A that may be used for a multi-level surgery. In this embodiment, superior eyelets 12 may be offset towards a first lateral end 100L from a centerline of implant 100A and inferior eyelets 22 may be offset towards a second lateral end 100L from the centerline of implant 100A. In this way, eyelets 12, 24 will not interfere with one another when used in a multi-level surgery, for example as shown in FIG. 18. As explained previously, any combination of any size shims 30 may be used to achieve a target alignment of the patients spine to adjust the spacing and inclination between a first vertebrae 1, second vertebrae 2, and third vertebrae 3 in the sagittal and coronal planes. In some embodiments, the eyelets 12, 22 may be staggered such that the implant 100 may be used in corpectomy procedure where at least one vertebrae, or a portion thereof, is removed from the patient.

Figure 19:
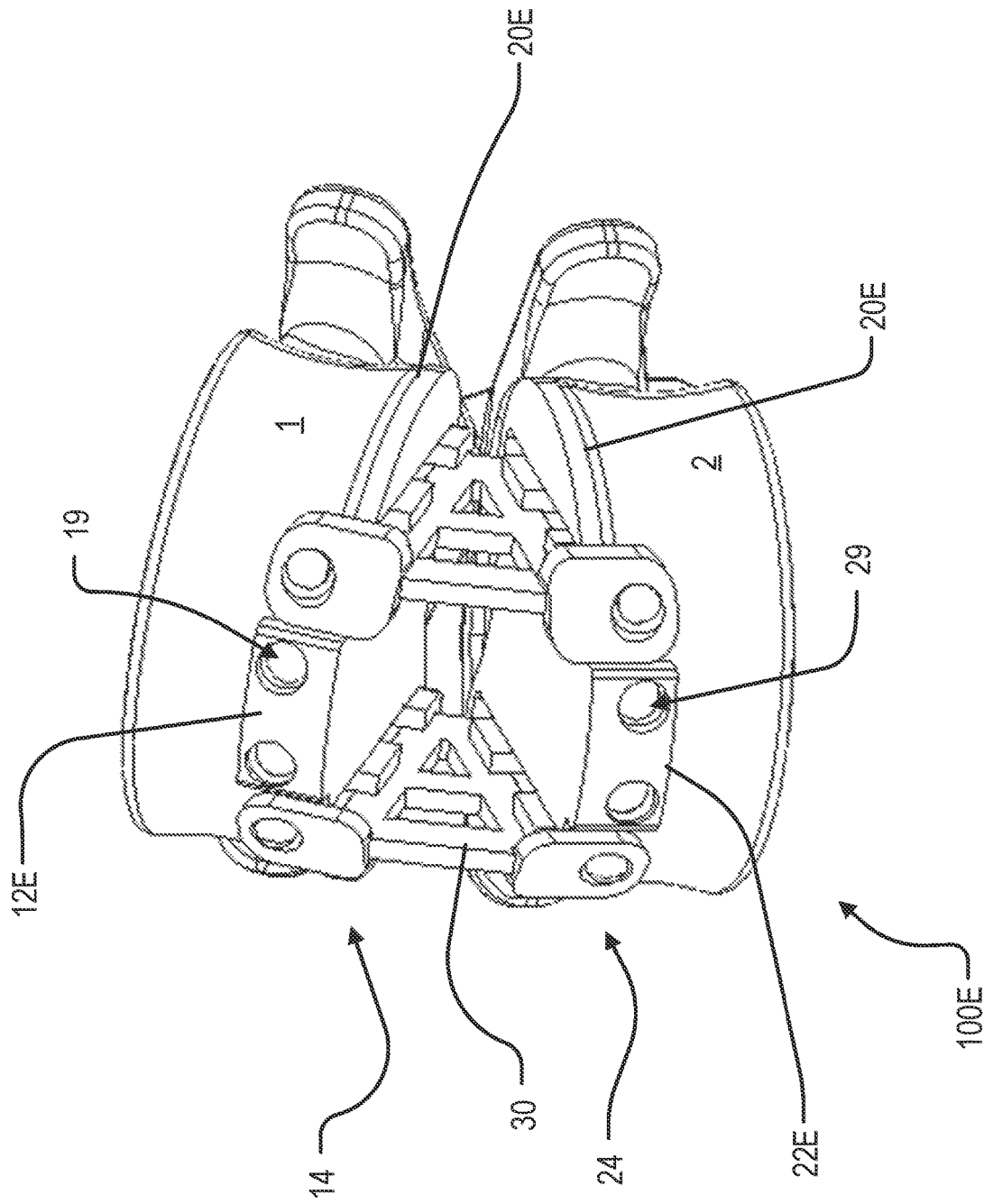
FIG. 19 is a perspective view of an alternate embodiment of an expandable implant.
Figure 20:
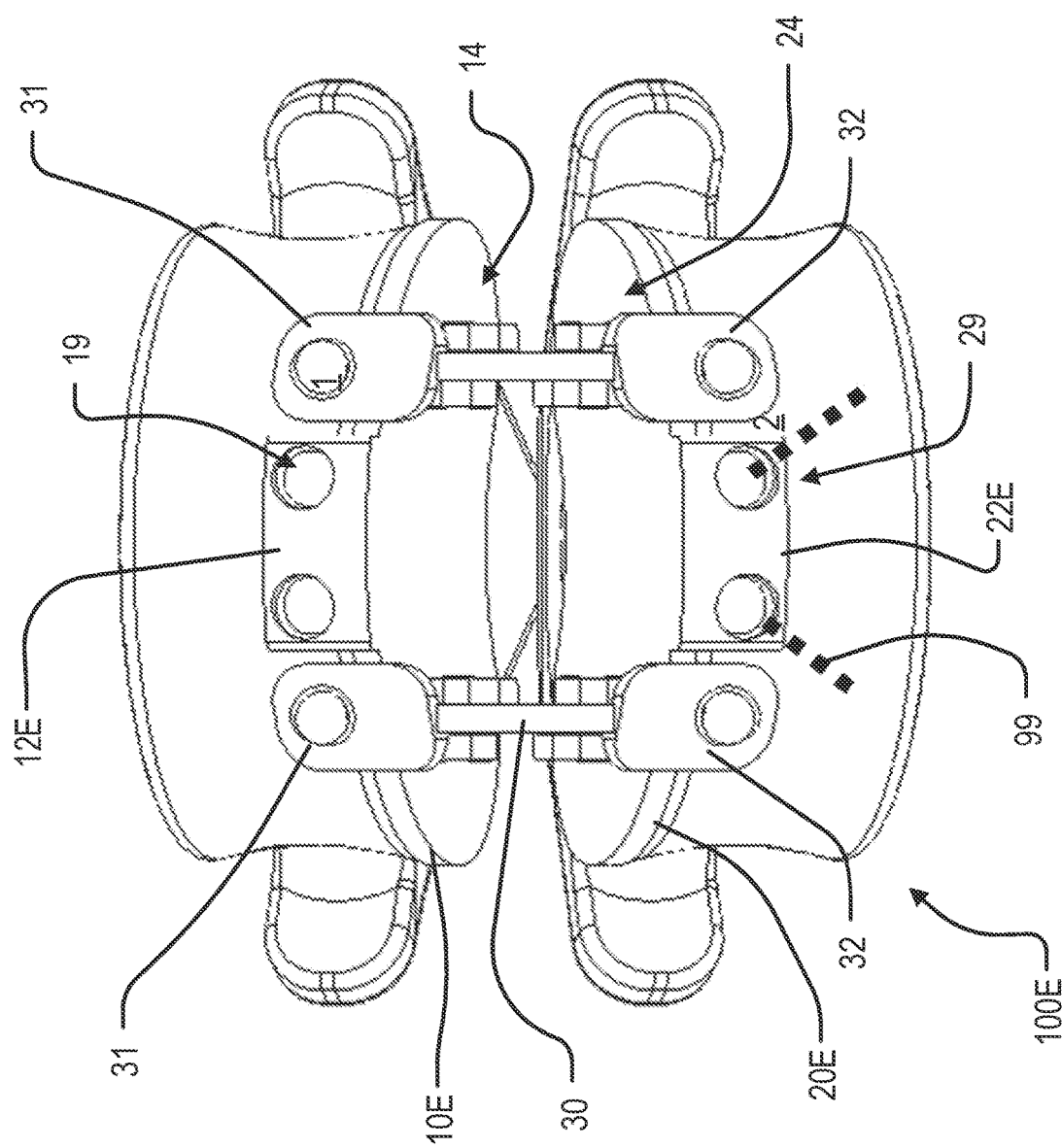
FIG. 20 is a front perspective view of the embodiment of FIG. 19.

FIG. 19 is a perspective view of an alternate embodiment of an expandable implant 100E; and FIG. 20 is a front perspective view of the embodiment of FIG. 19. Implant 100E may have the same, similar, and/or substantially the same components and functionality as previously explained. In this embodiment, superior endplate 10E may include a dual aperture eyelet 12E and the inferior endplate 20E may also include a dual aperture eyelet 22E. Eyelets 12E and 22E may therefore define bone screw apertures 19 and 29, respectively. In this embodiment, bone screw apertures 19, 29 may each define a target bone screw trajectory 99, for example. As shown with respect to bone screw apertures 29 and target bone screw trajectories 99, the inferior eyelet 22E may define a converging bone screw pattern. Similarly, the superior eyelet 12E may define a converging bone screw pattern. In some embodiments, the eyelets 12E, 22E may define a converging bone screw pattern and the eyelets 31, 32 of shims 30 may define a diverging screw pattern, for example. In this way, the pair of superior eyelets 31 may orient respective bone screws such that they diverge away from a centerline of implant 100, and the superior dual eyelet 12E may orient respective bone screws such that they converge towards a centerline of implant 100E. Similarly, the pair of inferior eyelets 32 may orient respective bone screws such that they diverge away from a centerline of implant 100, and the inferior dual eyelet 22E may orient respective bone screws such that they converge towards a centerline of implant 100.

Figure 21:
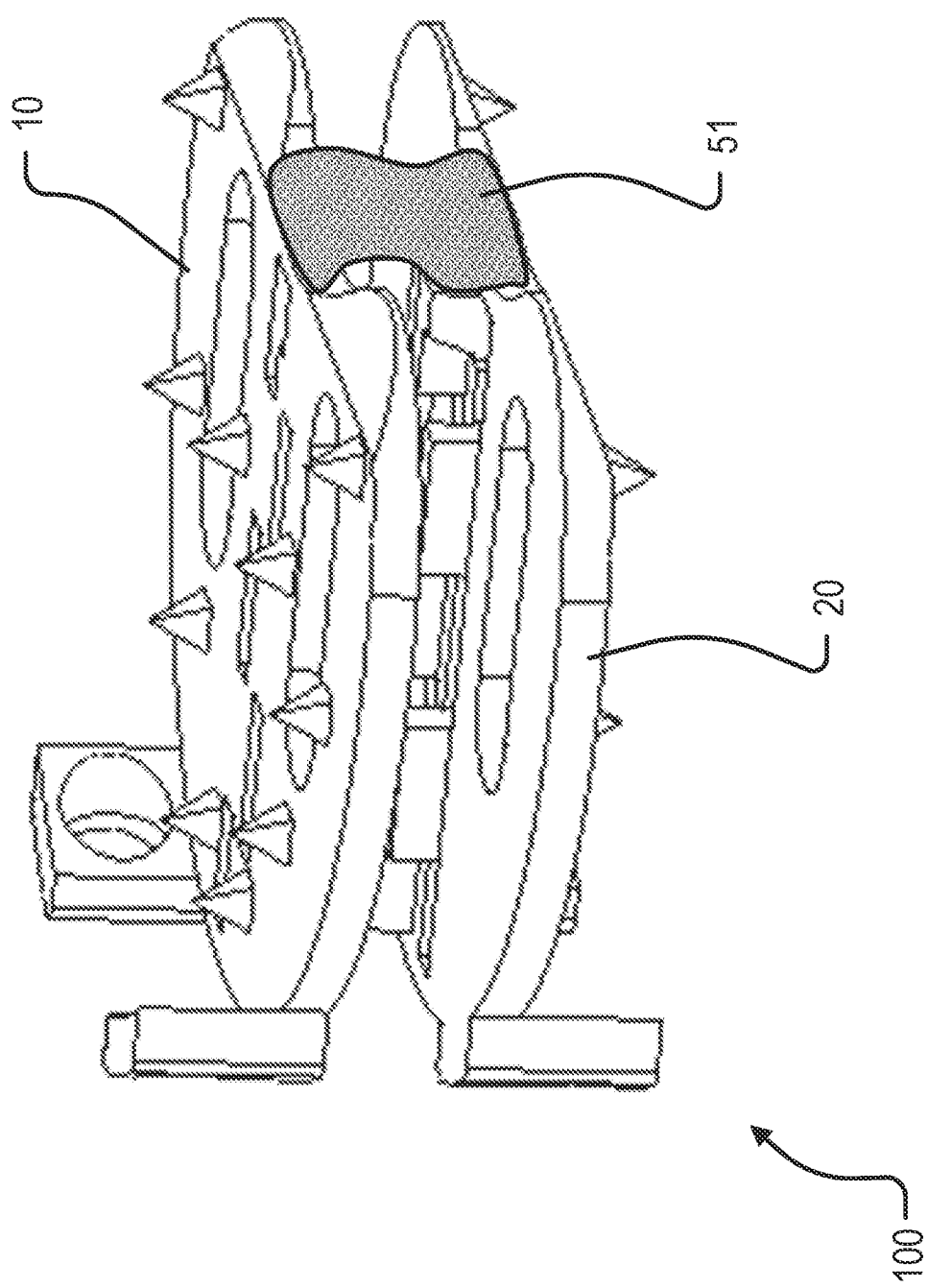
FIG. 21 is a first rear perspective view of an expandable implant.
Figure 22:
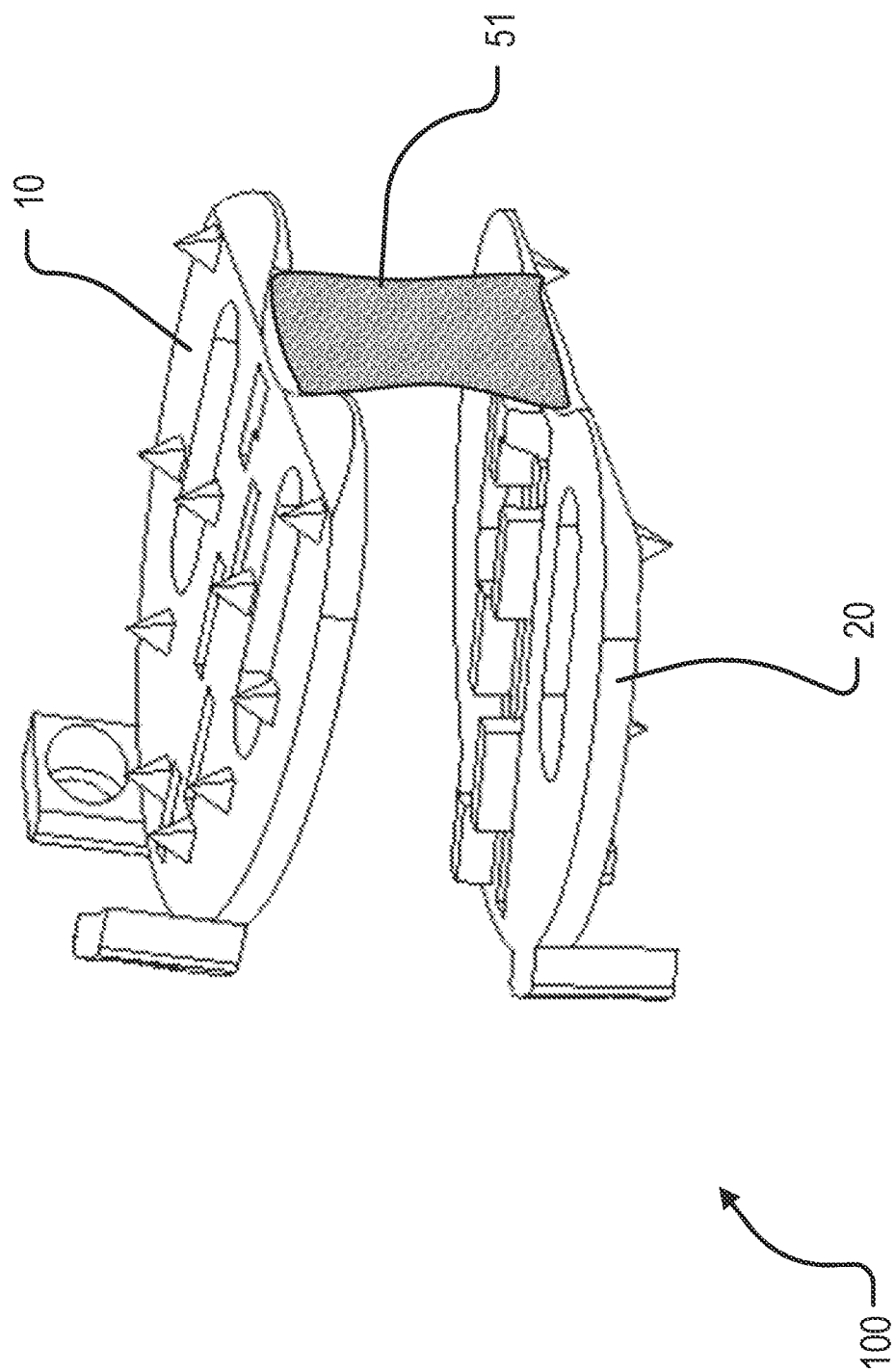
FIG. 22 is a second rear perspective view of an expandable implant.

FIG. 21 is a first rear perspective view of an expandable implant 100 including a coupling ribbon 51; and FIG. 22 is a second rear perspective view of an expandable implant 100 including the coupling ribbon 51. In the example embodiment, the superior endplate 10 and inferior endplate 20 are coupled together by ribbon 51 adjacent a distal end 100D of implant 100. The coupling ribbon may prevent the superior and inferior endplates 10, 20 from becoming loose and/or keep implant 100 together for shipping and assembly purposes. Additionally, in some embodiments coupling ribbon 51 may prevent an over expansion of implant 100 as a safety feature. Furthermore, coupling ribbon 51 may also provide a tensile support between the superior endplate 10 and inferior endplate 20 which may also facilitate in the prevention and/or suppression of injuries to the spine. Further still, coupling ribbon may function as a curtain wall to contain graft material within implant 100. Additionally, in various embodiments coupling ribbon 51 may define a portion of the posterior end or wall of implant 100, for example. Similarly, coupling ribbon 51 may be used as a supporting tension member, such as in the case of providing a discontinuous shims configured to function like a fulcrum as explained above. In a similar embodiment, a relatively tight fitting tension ribbon 51 may be disposed on the proximal end of implant 100 and a relatively tight fitting tension ribbon 51 may be disposed on the distal end of implant 100. In this embodiment, the tension ribbons 51 are disposed on opposite sides of the fulcrum/pivot point and may result in a relatively rigid implant used for stabilization of the segment. Additionally, in some embodiments, tension ribbon(s) 51 may be elastic such that they allow the implant 100 to elastically stretch, which may have the added advantage of providing a motion-sparing device that allows and/or facilitates a natural range of motion of a patient, or even a discrete subset of the natural range of motion of the patient as needed. In various embodiments, coupling ribbon 51 may wrap around at least a portion of the superior endplate 10 and/or inferior endplate 20. In at least one embodiment, coupling ribbon 51 wraps around both of the superior endplate 10 and inferior endplate 20 in a proximal-to-distal direction or alternatively in a widthwise direction, e.g., it wraps around the implant 100 in 360 degrees. In other embodiments, the coupling ribbon 51 may wrap around and/or have a width approximating (a) the length of the proximal end 100P of implant 100, (b) a width of either lateral end 100L of implant 100, (c) a distal end 100D of implant 100, (d) any combination of (a)-(c).

Figure 23:
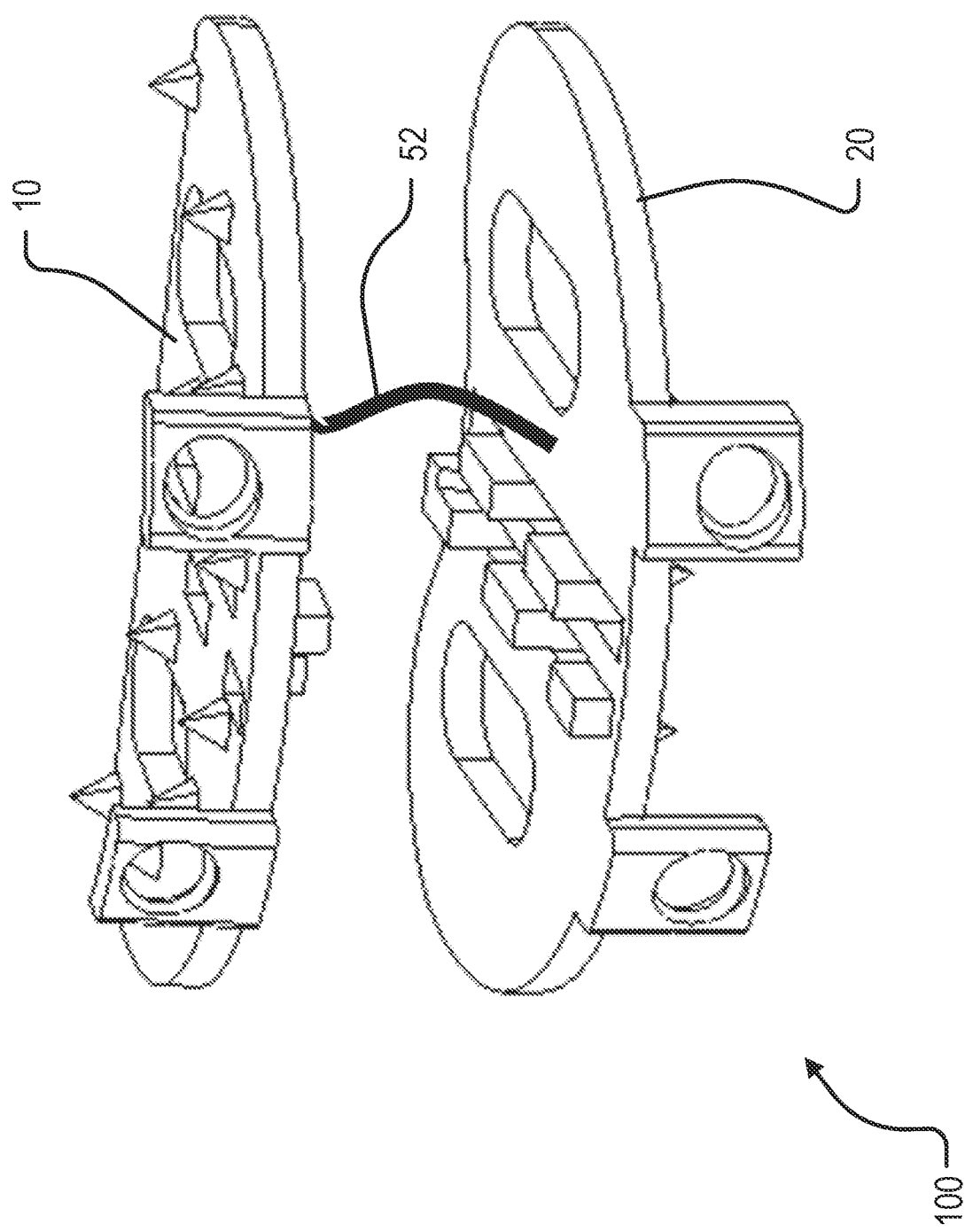
FIG. 23 is a perspective view of an expandable implant.

FIG. 23 is a perspective view of an expandable implant 100 including a coupling tether 52. In this embodiment, coupling tether 52 is coupled to the interior surface of superior endplate 10 and inferior endplate 20. Tether 52 may prevent the superior and inferior endplates 10, 20 from becoming loose and/or keep implant 100 together for shipping and assembly purposes. Additionally, in some embodiments coupling tether 52 may prevent an over expansion of implant 100 as a safety feature. Furthermore, coupling tether 52 may also provide a tensile support between the superior endplate 10 and inferior endplate 20 which may also facilitate in the prevention and/or suppression of injuries to the spine. In various embodiments, tether 52 may be a titanium cable that is spot welded to the superior and inferior endplates 10, 20, for example. In some embodiments, coupling tether 52 may be a turnbuckle and have the advantage of placing the implant in a compressed state such that is rigidly maintained and that internal forces are more evenly distributed throughout implant 100. In other embodiments, coupling tether 52 may be elastically deformable and undergo an elastic deformation when shims 30 are insert within implant thereby providing a biasing force urging the superior endplate 10 and inferior endplate 20 towards one another. Similarly as explained above with respect to tension ribbon 51, alternate embodiments of coupling tether 52 may also be used as a part of a tension member and/or as a motion-sparing device.

Figure 24:
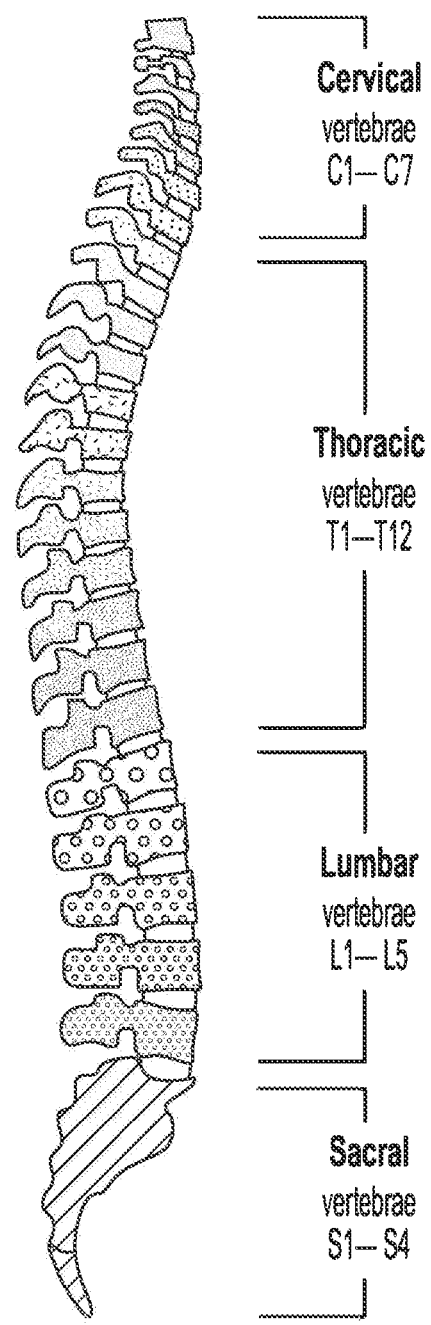
Figure 25:
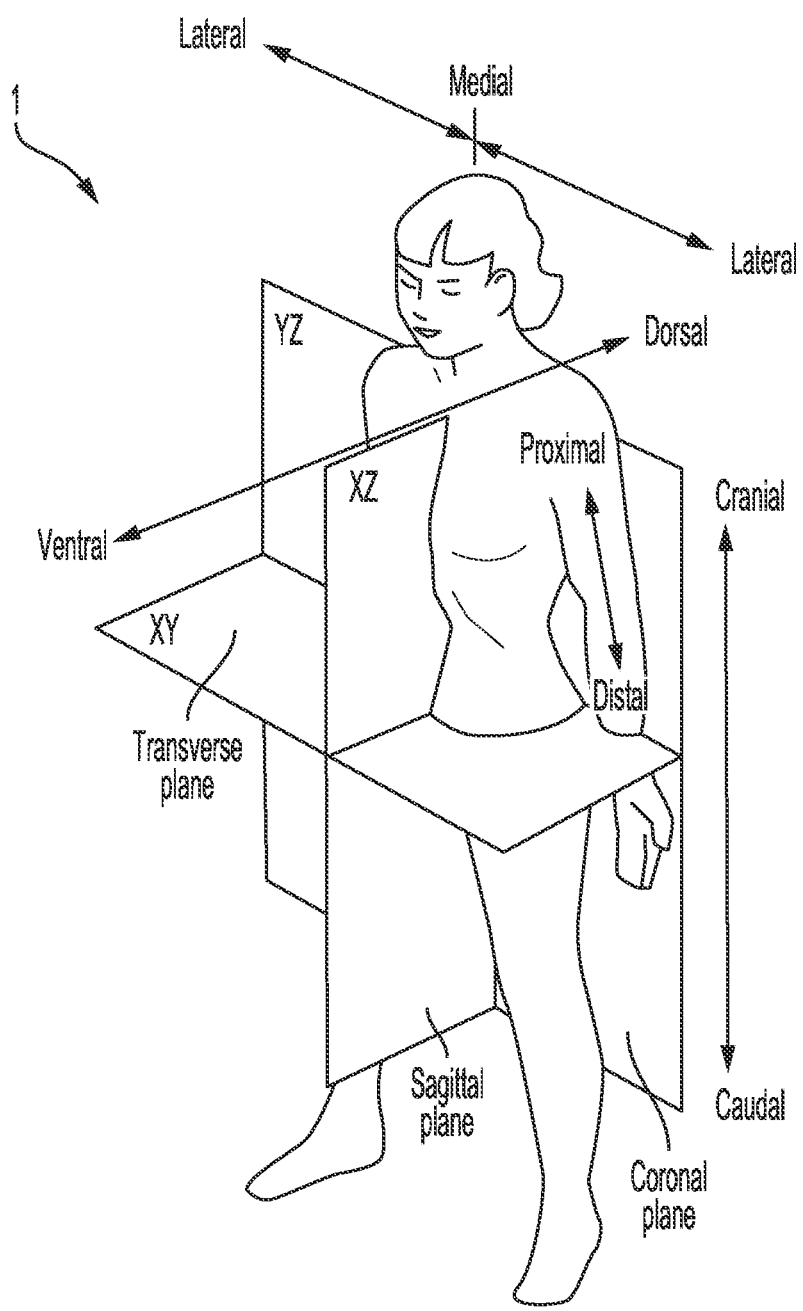
FIG. 25 is a reference drawing showing various planes and reference directions of which the various disclosed implant embodiments may move in or act in with respect to a patient.

FIG. 24 is a reference drawing showing the human spine of which various disclosed implant embodiments may be installed in. FIG. 25 is a reference drawing showing various planes and reference directions of which the various disclosed implant embodiments may move in or act in with reference to a patient 1.

In view of the disclosed embodiments, it shall be appreciated that the unconstrained nature of the endplates allows any combination of movements between the endplates, such as a relatively substantial amount of lordosis coupled with slight distraction, or a full distraction and lordosis type of adjustment, for example. Various embodiments may be sold as a kit with a range of shim sizes and configurations that a surgeon may select pre-operatively or during an operation to suit any particular patient need. Additionally, a footprint of any of the endplates may be adjusted in size and shape to suit the particular anatomy of a specific patient.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

What is claimed is:

1. An expandable implant movable between a collapsed position and an expanded position, comprising:
    a superior endplate including a first track on an interior surface thereof, the first track including a first plurality of protrusions, the first plurality of protrusions further comprises a first plurality of raised block structures and the first track further comprises a first plurality of apertures;
    an inferior endplate including a second track on an interior surface thereof, the second track including a second plurality of protrusions, the second plurality of protrusions further comprises a second plurality of raised block structures and the second track further comprises a second plurality of apertures; and
    a first shim having a superior bearing surface for directly contacting the first track between the first plurality of protrusions and supporting the superior endplate, and an inferior bearing surface for directly contacting the second track between the second plurality of protrusions and supporting the inferior endplate,
    wherein, in a collapsed position, the first track is aligned with the second track, the first plurality of raised block structures extends through the second plurality of apertures, and the second plurality of raised block structures extends through the first plurality of apertures,
    wherein, in an expanded position, the first shim defines a spacing and angle of inclination between the superior endplate and the inferior endplate, and
    wherein, in a side view, the superior bearing surface and inferior bearing surface form an acute angle defining the angle of inclination between the superior endplate and the inferior endplate.

2. The expandable implant of claim 1, wherein, in the collapsed position, the interior surface of the superior endplate contacts the interior surface of the inferior endplate.

3. The expandable implant of claim 1, wherein:
    the superior endplate further comprises a first eyelet defining a first bone screw aperture,
    the inferior endplate further comprises a second eyelet defining a second bone screw aperture, and
    the first eyelet extends in a superior direction from a proximal end of the superior endplate and the second eyelet extends in an inferior direction from a proximal end of the inferior endplate.

4. The expandable implant of claim 1, wherein the superior endplate comprises a first bone graft window and the inferior endplate comprises a second bone graft window.

5. The expandable implant of claim 1, wherein the first track extends in a proximal to distal direction about a centerline of the superior endplate and the second track extends in a proximal to distal direction about a centerline of the inferior endplate.

6. The expandable implant of claim 1, wherein the shim further comprises a blunt nose portion with chamfered ends and at least one eyelet opposite the blunt nose portion.

7. The expandable implant of claim 1, wherein the shim further comprises a blunt nose portion at a distal end thereof, a stabilizing strut at a medial position thereof extending between the superior bearing surface and the inferior bearing surface, and a superior eyelet and inferior eyelet at a proximal end thereof.

8. The expandable implant of claim 1, wherein a footprint of the implant is designed for use in an anterior lumbar interbody fusion procedure.

9. The expandable implant of claim 1, wherein a footprint of the implant is designed for use in a transforaminal lumbar interbody fusion procedure.

10. The expandable implant of claim 1, wherein a footprint of the implant is designed for use in a lateral lumbar interbody fusion procedure.

11. An expandable implant movable between a collapsed position and an expanded position, comprising:
    a superior endplate including a first track having a first plurality of protrusions and a second track having a second plurality of protrusions disposed on an interior surface thereof, the first plurality of protrusions further comprises a first plurality of raised block structures and the first track further comprises a first plurality of apertures, and the second plurality of protrusions further comprises a second plurality of raised block structures and the second track further comprises a second plurality of apertures;
    an inferior endplate including a third track having a third plurality of protrusions and a fourth track having a fourth plurality of protrusions disposed on an interior surface thereof, the third plurality of protrusions further comprises a third plurality of raised block structures and the third track further comprises a third plurality of apertures, and the fourth plurality of protrusions further comprises a fourth plurality of raised block structures and the fourth track further comprises a fourth plurality of apertures; and
    a first shim having a superior bearing surface for directly contacting the first track between the first plurality of protrusions and supporting the superior endplate and an inferior bearing surface for directly contacting the third track between the third plurality of protrusions and supporting the inferior endplate, a second shim having a superior bearing surface for directly contacting the second track between the second plurality of protrusions and supporting the superior endplate and an inferior bearing surface for directly contacting the fourth track between the fourth plurality of protrusions and supporting the inferior endplate, wherein, in a collapsed position, the first track is aligned with the third track and the second track is aligned with the fourth track, and the first plurality of raised block structures extends through the third plurality of apertures and the second plurality of raised block structures extends through the fourth plurality of apertures, wherein, in an expanded position, the first shim is disposed within the first track and third track and the second shim is disposed within the second track and fourth track, wherein the first and second shims define a spacing and an angle of inclination between the superior endplate and the inferior endplate, wherein, in a side view, the superior bearing surface of the first shim and the inferior bearing surface of the first shim form a first acute angle, wherein, in a side view, the superior bearing surface of the second shim and the inferior bearing surface of the second shim for a second acute angle, and wherein the first acute angle and the second acute angle together define the angle of inclination between the superior endplate and the inferior endplate.

12. The expandable implant of claim 11, wherein in the collapsed position the interior surface of the superior endplate contacts the interior surface of the inferior endplate.

13. The expandable implant of claim 11, wherein:
the superior endplate further comprises a first eyelet defining a first bone screw aperture,
the inferior endplate further comprises a second eyelet defining a second bone screw aperture, and
the first eyelet extends in a superior direction from a proximal end of the superior endplate and the second eyelet extends in an inferior direction from a proximal end of the inferior endplate.

14. The expandable implant of claim 11, wherein:
the superior endplate further comprises a first dual eyelet defining a first bone screw aperture and a second bone screw aperture,
the inferior endplate further comprises a second dual eyelet defining a third bone screw aperture and a fourth bone screw aperture,
the first dual eyelet defines a first diverging bone screw trajectory with respect to the first and second bone screw apertures, and
the second dual eyelet defines a second diverging bone screw trajectory with respect to the third and fourth bone screw apertures.

15. The expandable implant of claim 11, wherein:
the first shim has a first height at a proximal end thereof and the second shim has a second height at a distal end thereof, and
the first height being greater than the second height.

16. The expandable implant of claim 15, wherein:
the first track and the second track are disposed at substantially equal distances from and on opposite sides of a centerline of the superior endplate,
the third track and the fourth track are disposed at substantially equal distances from and on opposite sides of a centerline of the inferior endplate.

17. The expandable implant of claim 11, wherein a footprint of the implant is designed for use in an anterior lumbar interbody fusion procedure and the implant is adjustable in the sagittal plane and in the coronal plane by adjusting a relative size and shape of the first shim and second shim.

18. The expandable implant of claim 11, wherein at least one of the first shim and second shim further comprises a blunt nose portion with chamfered ends and at least one eyelet opposite the blunt nose portion.

19. An expandable implant movable between a collapsed position and an expanded position, comprising:
a superior endplate including a first track on an interior surface thereof, the first track including a first plurality of protrusions;
an inferior endplate including a second track on an interior surface thereof, the second track including a second plurality of protrusions; and
a shim having a superior bearing surface for directly contacting the first track between the first plurality of protrusions and supporting the superior endplate, and an inferior bearing surface for directly contacting the second track between the second plurality of protrusions and supporting the inferior endplate,
wherein the shim further comprises a blunt nose portion with chamfered ends and a superior eyelet opposite the blunt nose portion,
wherein, in a collapsed position, the first track is aligned with the second track,
wherein, in an expanded position, the first shim defines a spacing and angle of inclination between the superior endplate and the inferior endplate, and
wherein, in a side view, the superior bearing surface and inferior bearing surface form an acute angle defining the angle of inclination between the superior endplate and the inferior endplate.

20. The expandable implant of claim 19, wherein the superior eyelet is a closed eyelet.

* * * * *